US010429359B2

(12) United States Patent
Eriksson et al.

(10) Patent No.: US 10,429,359 B2
(45) Date of Patent: Oct. 1, 2019

(54) AUTOMATED MULTI-STEP PURIFICATION SYSTEM

(71) Applicant: GE Healthcare Bio-Sciences AB, Uppsala (SE)

(72) Inventors: Christer Olof Eriksson, Uppsala (SE); Nils Norrman, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 213 days.

(21) Appl. No.: 15/116,940

(22) PCT Filed: Feb. 13, 2015

(86) PCT No.: PCT/EP2015/053117
§ 371 (c)(1),
(2) Date: Aug. 5, 2016

(87) PCT Pub. No.: WO2015/121425
PCT Pub. Date: Aug. 20, 2015

(65) Prior Publication Data
US 2017/0153210 A1     Jun. 1, 2017

(30) Foreign Application Priority Data
Feb. 14, 2014   (SE) ...................................... 1450174

(51) Int. Cl.
*G01N 30/04*     (2006.01)
*B01D 15/34*     (2006.01)
(Continued)

(52) U.S. Cl.
CPC ........... *G01N 30/04* (2013.01); *B01D 15/125* (2013.01); *B01D 15/16* (2013.01);
(Continued)

(58) Field of Classification Search
CPC ...... B01D 2256/12; B01D 2259/40005; B01D 2259/4533; B01D 53/0446; B01D 53/047;
(Continued)

(56) References Cited

U.S. PATENT DOCUMENTS 6,318,157 B1 * 11/2001 Corso .................. G01N 30/466
                                              210/198.2
6,344,172 B1 *  2/2002 Afeyan ................ G01N 30/461
                                              210/198.2
(Continued)

FOREIGN PATENT DOCUMENTS

CN         103221105 A      7/2013
CN         103562145 A      2/2014
(Continued)

OTHER PUBLICATIONS

International Preliminary Report on Patentability Received for PCT Application No. PCT/EP2015/053117, dated Aug. 25, 2016, 8 Pages.
(Continued)

*Primary Examiner* — Randy W Gibson
*Assistant Examiner* — Gedeon M Kidanu
(74) *Attorney, Agent, or Firm* — Wood IP LLC

(57) ABSTRACT

Automated two step chromatography purification system comprising a, system controller, a capture flow path comprising at least one pump, an elution flow path comprising at least one pump, and a valve arrangement for selective connection of two capture columns to the capture flow path and the elution flow path respectively such that both flow paths may be operated simultaneously and in parallel.

20 Claims, 17 Drawing Sheets

(51) Int. Cl.
*G01N 30/46* (2006.01)
*B01D 15/12* (2006.01)
*B01D 15/16* (2006.01)
*B01D 15/18* (2006.01)
*B01D 15/20* (2006.01)
*B01D 15/38* (2006.01)
*G01N 30/88* (2006.01)

(52) U.S. Cl.
CPC ..... *B01D 15/1871* (2013.01); *B01D 15/1885* (2013.01); *B01D 15/203* (2013.01); *B01D 15/34* (2013.01); *B01D 15/3804* (2013.01); *G01N 30/461* (2013.01); *G01N 30/468* (2013.01); *B01D 15/3809* (2013.01); *G01N 2030/8831* (2013.01)

(58) Field of Classification Search
CPC ............ B01D 15/1864; B01D 15/361; B01D 15/362; B01D 15/363; B01D 15/3804; B01D 15/125; B01D 15/16; B01D 15/1871; B01D 15/1885; B01D 15/203; B01D 15/34; G01N 2030/8831; G01N 30/04; G01N 30/461; G01N 30/467; G01N 30/468; G01N 30/96; G01N 2030/202; G01N 30/20; G01N 2030/201; G01N 35/1097; G01N 2030/326; G01N 30/22; G01N 30/32; G01N 30/36
See application file for complete search history.

(56) References Cited

U.S. PATENT DOCUMENTS

| | | | |
|---|---|---|---|
| 7,566,395 | B2 | 7/2009 | Lundblad et al. |
| 8,257,586 | B2* | 9/2012 | Dehmer .................. G01N 30/20 210/198.2 |
| 2005/0061722 | A1* | 3/2005 | Takao ........................ F04B 9/02 210/137 |
| 2006/0030696 | A1* | 2/2006 | Bonnerjea ................ C07K 1/22 530/387.1 |
| 2008/0053901 | A1* | 3/2008 | Mierendorf ........ B01D 15/1842 210/635 |
| 2008/0307861 | A1* | 12/2008 | Quinn .................... G01N 30/34 73/61.56 |
| 2010/0058841 | A1* | 3/2010 | Wilen .................. F16K 11/0743 73/61.56 |
| 2011/0240899 | A1* | 10/2011 | Wilen .................. F16K 11/0743 251/304 |
| 2012/0103887 | A1* | 5/2012 | Maeda ................ F16K 11/0743 210/198.2 |
| 2012/0145937 | A1* | 6/2012 | Richman ............. F16K 11/0743 251/304 |
| 2014/0251911 | A1* | 9/2014 | Skudas .............. B01D 15/1864 210/656 |
| 2015/0165343 | A1* | 6/2015 | Geng .................... G01N 30/462 530/417 |
| 2015/0233479 | A1* | 8/2015 | Bjemulf ................ F16K 11/076 137/625.23 |

FOREIGN PATENT DOCUMENTS

| | | |
|---|---|---|
| CN | 102574026 B | 10/2015 |
| CN | 102574911 B | 6/2017 |
| EP | 2682168 A1 | 1/2014 |
| EP | 3105580 A1 | 12/2016 |
| JP | 2007514153 A | 5/2007 |
| JP | 2010271300 A | 12/2010 |
| WO | 9307168 A2 | 4/1993 |
| WO | 2008/157426 A1 | 12/2008 |
| WO | 2011/017514 A1 | 2/2011 |
| WO | 2011/037522 A1 | 3/2011 |
| WO | 2012/074481 A1 | 6/2012 |
| WO | 2013/050104 A1 | 4/2013 |
| WO | 2015/121425 A1 | 8/2015 |

OTHER PUBLICATIONS

Office Action Received for Chinese Patent Application No. 201580008706.5, dated May 19, 2017, 24 pages (14 Pages of English Translation + 10 Pages official copy).

International Search Report and Written Opinion regarding International Application No. PCT/EP2015/053117, dated May 12, 2015, 11 pages.

International-Type Search Report regarding SE Application No. 1450174-6, dated Aug. 28, 2014, 8 pages.

Japan Notice of Preliminary Rejection for Japanese Patent Application No. 2016-550709, dated Jan. 8, 2019, 6 pages.

* cited by examiner

AUTOMATED MULTI-STEP PURIFICATION SYSTEM

CROSS-REFERENCE TO RELATED APPLICATIONS

This application is a filing under 35 U.S.C. 371 of international application number PCT/EP2015/053117, filed Feb. 13, 2015, which claims priority to SE application number 1450174-6, filed Feb. 14, 2014, the entire disclosures of each of which are hereby incorporated by reference.

FIELD OF THE INVENTION

The present invention relates to multi-step chromatography purification and more specifically to automated multi-step chromatography purification system with two or more purification segments for performing purification of target molecules from separate feed sources in isolation with respect to each other.

BACKGROUND

In drug research of today there is an increased demand to purify many proteins in short time. However, protein purification is time consuming and it requires a lot of manual work.

Proteins e.g. in the form of therapeutic antibodies represent one of the fastest growing segments in the pharmaceutical market. The growth of the segment has necessitated development of new efficient and cost saving platforms for the preparation and analysis of early candidates for faster and better antibody selection and characterization. Typically, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the byproducts of the cells themselves to a purity sufficient for preparation and analysis poses a formidable challenge.

Procedures for purification of proteins from cell debris initially depend on the site of expression of the protein. Some proteins are caused to be secreted directly from the cell into the surrounding growth media; others are made intracellular. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by centrifugation or by filtration. The same problem arises, although on a smaller scale, with directly secreted proteins due to the natural death of cells and release of intracellular host cell proteins in the course of the protein production run.

As a consequence, typical purification processes that are presently used include the following steps:
  cell lysis to recover an intracellular protein or recovery of a protein from the media in case of a secreted protein
  removal of cellular debris using e.g. differential centrifugation or filtration to obtain a clarified sample containing the protein of interest
  use of a variety of chromatography media in a multi-step process to separate the protein of interest from other proteins and the various other impurities in the sample.

The chromatographic techniques typically separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Ion-exchange chromatography, named for the exchangeable counterion, is a procedure applicable to purification of ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. In typical protein purification using ion exchange chromatography, a mixture of many proteins derived from a host cell, such as in mammalian cell culture, is applied to an ion-exchange column. After non-binding molecules are washed away, conditions are adjusted, such as by changing pH, counter ion concentration and the like in step- or gradient-mode, to release from the solid phase a non-specifically retained or retarded ionized protein of interest and separating it from proteins having different charge characteristics.

Anion exchange chromatography involves competition of an anionic molecule of interest with the negative counter ion for interaction with a positively charged molecule attached to the solid phase matrix at the pH and under the conditions of a particular separation process. By contrast, cation exchange chromatography involves competition of a cationic molecule of interest with the positive counter ion for a negatively charged molecule attached to the solid phase matrix at the pH and under the conditions of a particular separation process. Mixed mode ion exchange chromatography involves the use of a combination of cation and anion exchange chromatographic media in the same step. In particular, "mixed-mode" refers to a solid phase support matrix to which is covalently attached a mixture of cation exchange and/or anion exchange and hydrophobic interaction moieties.

Affinity chromatography, which exploits a specific structurally dependent (i.e., spatially complementary) interaction between the protein to be purified and an immobilized capture agent, is a standard purification option for some proteins, such as antibodies. Protein A, for example, is a useful adsorbent for affinity chromatography of proteins, such as antibodies, which contain an Fc region. Protein A is a 41 kD cell wall protein from *Staphylococcus aureas* which binds with a high affinity (about $10^{-8}$M to human IgG) to the Fc region of antibodies.

Further chromatographic methods are Hydroxyapatite chromatography or Hydrophobic interaction chromatography (HIC). More detailed descriptions of protein purification and chromatography processes may be found in a series of handbooks in the field provided by GE Healthcare Life Sciences, including: Affinity Chromatography, Antibody Purification, strategies for protein purification etc. all which are incorporated by reference herein.

Consequently, typical purification processes one or more centrifugation and filtration steps as well as at least 2 chromatographic separation techniques such as affinity chromatography (AC), gel permeation chromatography (GPC), ion exchange chromatography (IEC), hydrophobic interaction chromatography (HIC), reversed phase chromatography (RPC), and normal phase chromatography (NPC). Usually each of named techniques requires different operation (buffer, pH, conductivity) conditions that lead to sample preparation before chromatographic separation implementation.

As mentioned, a chromatography purification protocol may comprise one or more purification steps, and in one example a protocol comprises three purification steps commonly referred to as capture, intermediate purification, and polishing. Table 1 illustrates relative characteristics for a selection of different chromatography purification techniques and relative use in the different purification steps of a three step protocol. When designing a chromatography purification protocol there are four important performance parameters to consider when planning each purification step: resolution, capacity, speed, and recovery. Optimization of any one of these four parameters can be achieved only at the expense of the others, and each purification step will be a compromise. The importance of each parameter will vary depending on the purpose of each purification step, e.g. whether a purification step is used for capture, intermediate purification, or polishing or the like. Purification methods should be selected and optimized to meet the objectives for each purification step. Even though recovery may not be the key parameter to be optimized, it will nonetheless be of concern in any preparative situation, especially for production of a high-value product, and it is then important to assay for recovery during optimization of the capture step.

TABLE 1

| Method | Typical. | | Purification.. | | |
| --- | --- | --- | --- | --- | --- |
| | Resolutio | Capacity | Capture | Intermedi | Polishing |
| AC | +++ | +++ | +++ | ++ | + |
| | or | or | | | |
| IMAC | +++ | ++ | +++ | ++ | + |
| GF | ++ | + | + | | +++ |
| IEX | +++ | +++ | +++ | +++ | +++ |
| HIC | +++ | ++ | ++ | +++ | +++ |
| Chromato- | +++ | + | | | ++ |
| RPC | +++ | ++ | | + | ++ |

The optimal balance between capacity and resolution must be defined for each case. As in a capture stage, selectivity will be important, not only to achieve high binding capacity for the target molecule. However, in contrast to most capture steps, selectivity during elution is important and is usually achieved by applying a continuous gradient or a multi-step elution procedure.

In addition to the different selectivities available through the various purification methods, the purification efficiency depends strongly on the selection of different chromatography media available for each method. The efficiency, flow resistance, selectivity, and capacity differ between media. The particle size of the medium strongly affects efficiency and flow resistance.

A medium with large beads give columns with low efficiency (the peaks are broad) and low backpressure, whereas small beads give high efficiency and high backpressure. Early in the purification process (e.g., the capture stage) high speed is often required because the sample volume is large and the sample quickly needs to be stabilized. There is less focus on the resolution. Chromatography media with large particles should be selected that give low backpressure at high flow rates. In the polishing stage focus is put on high purity, which can be obtained with chromatography media with high efficiency, that is, small beads. These media give higher backpressure that may require lower flow rates and columns that resist high pressure. These limitations are acceptable because the sample volume and amounts in this stage are smaller.

Simple batch chromatography technique is well accepted both in lab scale purification of proteins and in industrial applications; however this technology is labor intensive, expensive due to long processing times and high operation costs (e.g. large solvent amounts, expensive resins and hardware). This technique is also sensitive to operational conditions (e.g. product titer, residence time and feeding rate (product losses starting from 80% dynamic binding capacity values). Some alternative semi-continuous technologies were developed as well, meaning that they connect two or three different chromatography modes, such as WO 2011/037522 discloses a separation system comprising at least two separation units which are connected outlet to inlet. All columns are connected in line.

WO 2011/017514 discloses the combination of an affinity chromatography step and two ion exchange chromatography steps without the need for holding tanks or buffer exchange steps.

WO9307168 discloses one example of a prior art automated chromatography system for the essentially continuous separation and analysis of one protein, which includes sample input means, a first liquid chromatography column, a multiport injection valve connecting the sample input means to the column, pump means for providing variable pressure delivery of a solution to the column via the multiport valve, and program means for specifying a sequence of system control programs.

But none of these allow one to have a continuous feed. WO2013050104 discloses a prior art automated industrial scale chromatography system capable of running a continuous chromatography process which only needs three separation columns. The process is a two-step procedure comprising two chromatographic steps. The first chromatographic step (capture) is performed alternating and sequentially on preferably two separation columns; the second chromatographic step (polishing) is performed, also sequentially, on the third column. But neither this nor the above automated purification systems enables purification of a plurality of different samples in an automated and efficient manner using one and the same system.

Cleaning-in-place (CIP) of chromatography media (resins) is important for the integrity and safety of the final biopharmaceutical product. Depending on the source of the feed material, various types of impurities, if not removed, may be trapped in the chromatography medium and cause carryover from one cycle to the next. That carryover material may be product or product variants.

SUMMARY OF THE INVENTION

The object of the invention is to provide a chromatography purification system, which system overcomes one or more drawbacks of the prior art. This is achieved by the chromatography purification system as defined in the independent claim.

One benefit with the present chromatography purification system is that it allows unattended purification of a plurality of different target molecules directly from cell culture in an efficient manner.

A more complete understanding of the present invention, as well as further features and advantages thereof, will be obtained by reference to the following detailed description and drawings.

BRIEF DESCRIPTION OF THE DRAWINGS

FIGS. 4a-4c schematically show a two-step purification process.

DETAILED DESCRIPTION OF EMBODIMENTS OF THE INVENTION

Figure 1:
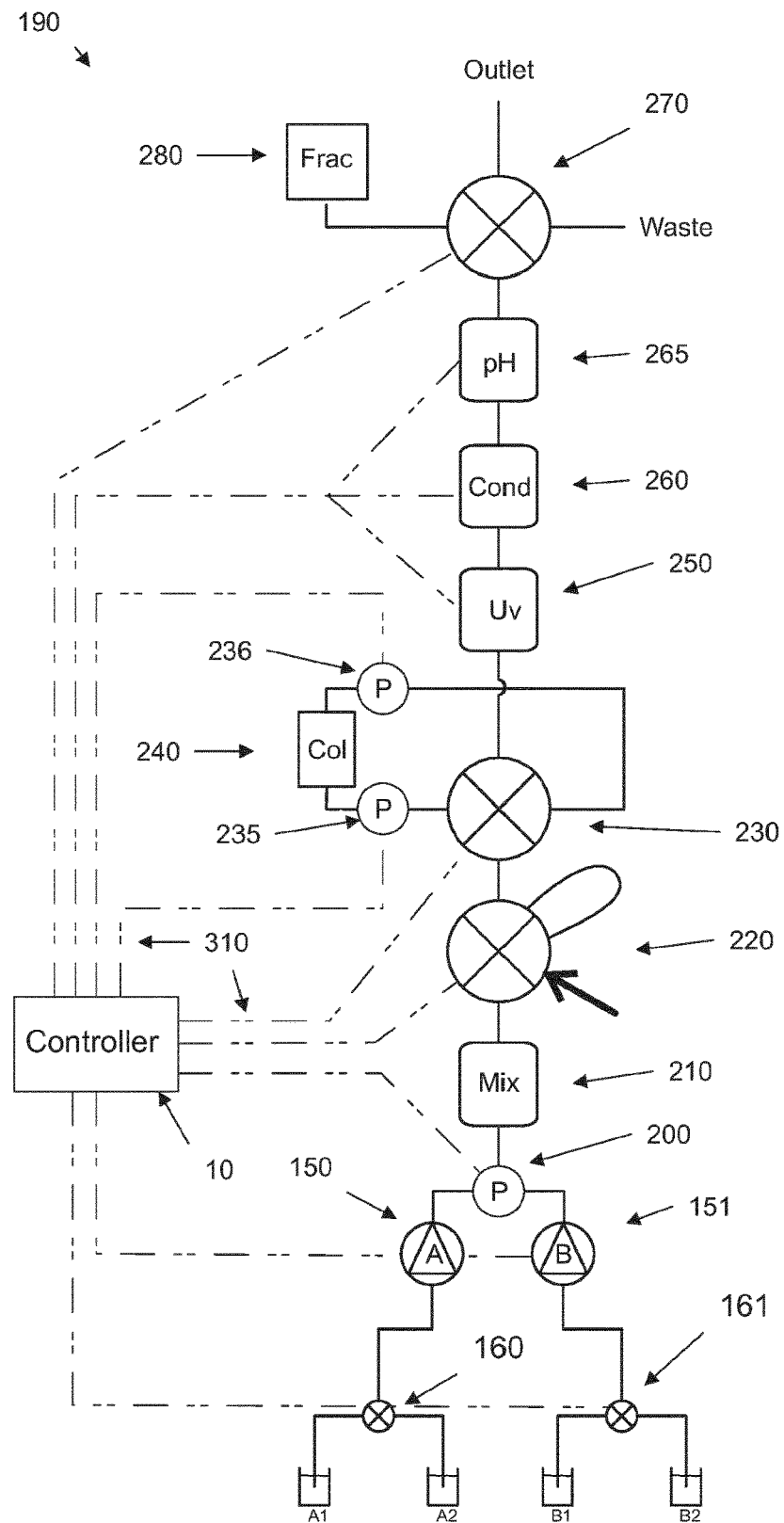
FIG. 1 schematically shows one embodiment of a chromatography system

FIG. 1 schematically shows one embodiment of a chromatography system 190 comprising:
- two 3-way input-valves 160 and 161, arranged to select the input fluid from fluid sources A1, A2, B1, B2
- two system pumps 150 and 151
- a pressure sensor 200 for registering the system pressure in the flow path after the system pumps,
- a mixer 210 to ensure appropriate mixing of the fluids supplied by the pumps,
- an injection valve 220 for injecting a sample into the fluid path,
- a column connection valve 230 for selectively connecting/disconnecting a column 240 in the fluid path.
- a pre-column pressure sensor 235 and a post-column pressure sensor 236
- an ultraviolet (UV) monitor 250 for detecting the output from the column.
- a conductivity monitor 260,
- a pH monitor 265,
- an output selection valve 270 with two or more output positions, e.g. connected to a fraction collector 280, a waste receptacle or the like and
- a system controller 10 connected to pumps and valves for controlling the liquid flow through the system, and to sensors and monitors for monitoring the flow, connections being illustrated by dotted lines 310.

The chromatography system of FIG. 1 represents a general example of how a chromatography system may be designed, and other embodiments may be of different design comprising two or more of some components and potentially lack some of said components. According to one embodiment, the chromatography system is a liquid chromatography system.

FIGS. 2a-2d schematically disclose a valve 10 that e.g. may be used in a chromatography system according to above. The valve 10 is a rotary valve with a stator with ports 131a, 132s, 133a and 134a, and a rotor with grooves 140, 141a and 141b (shown as dotted lines) formed in the surface facing the stator. The valve 10 is disclosed more in detail in the pending patent application PCT/SE2013/050985 which is incorporated herein by reference.

Figure 2A:
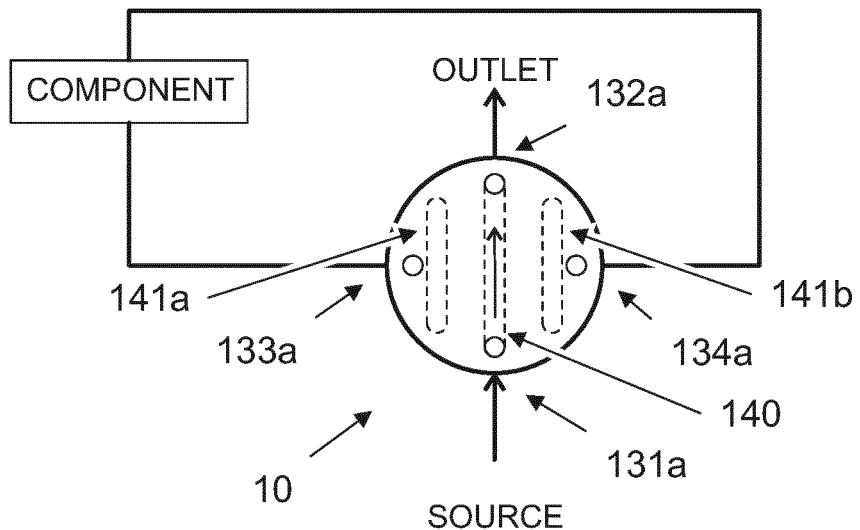
FIGS. 2a to 2d shows a schematic view of an embodiment of the rotary valve with the rotor positioned at different rotor positions.

In the first rotor position, as shown in FIG. 2a, the valve 10 is arranged to bypass the component ports 133a and 134a. The fluid flow enters the inlet port 131a, goes via the first orifice 131b through the diagonal rotor groove 140 and exits the valve through the outlet port 132a (via the second orifice 132b). The other ports and grooves of the valve are not active in the first rotor position, i.e. the component is bypassed.

Figure 2B:
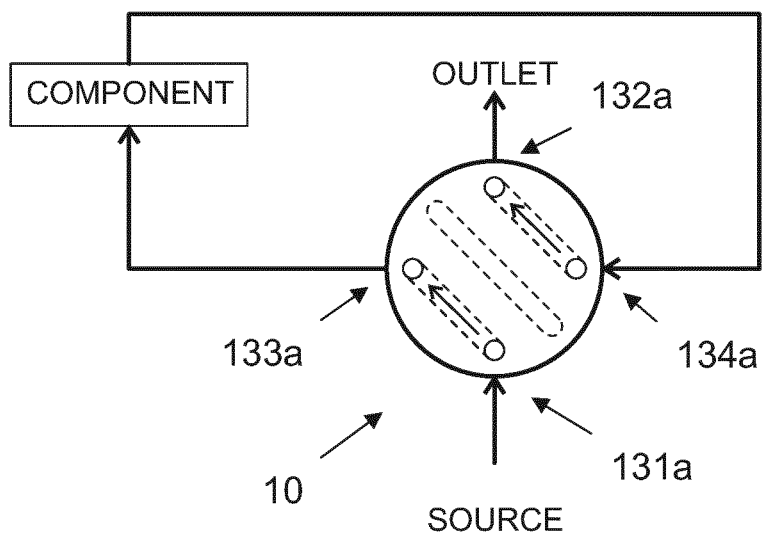

FIG. 2b shows the valve 10 in a second rotor position wherein the interconnection paths in the rotor 12 interconnect the inlet port 131a with the component feed port 133a and the component return port 134a with the outlet port 132a. In this rotor position, the component is connected into the fluid flow in a forward flow connection. More specifically, the parallel groove 141a interconnects the valve orifice 131b of the inlet port and the valve orifice 133b of the component feed port 133a, while the other parallel groove 141b interconnects the valve orifice 134b of the component return port 134a and the valve orifice 132b of the outlet port 132a.

Figure 2C:
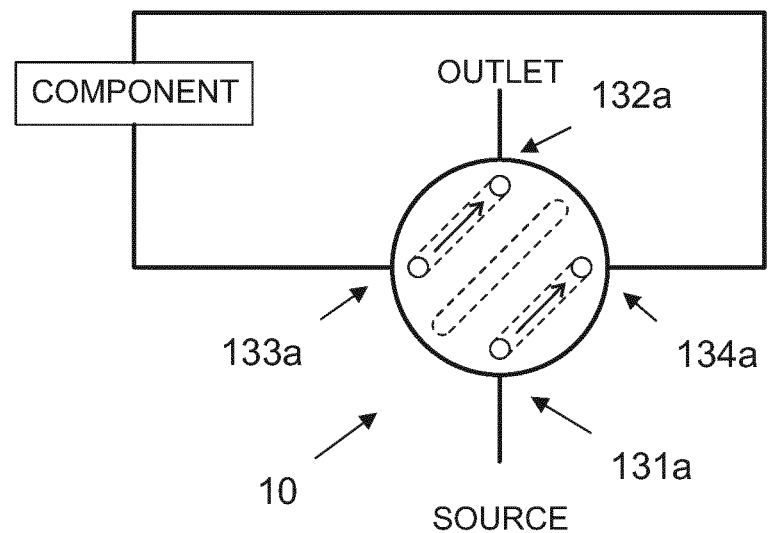

FIG. 2c shows the valve 10 in a third rotor position wherein the interconnection paths in the rotor 12 interconnect the inlet port 131a with the component return port 134a and the component feed port 133a with the outlet port 132a. In this rotor position, the component is connected into the fluid flow in a reversed flow connection. More specifically, the parallel groove 141a interconnects the valve orifice 131b of the inlet port and the valve orifice 134b of the component return port 134a, while the other parallel groove 141b interconnects the valve orifice 133b of the component feed port 133a and the valve orifice 132b of the outlet port 132a.

Figure 2D:
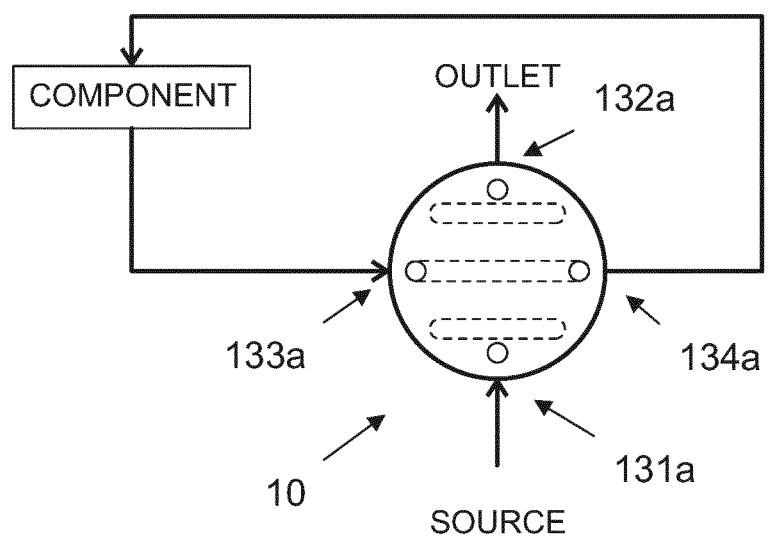

FIG. 2d shows the valve 10 in a fourth rotor position wherein the interconnection paths in the rotor 12 interconnect the component feed port 133a with the component return port 134a whereby the flow path between the main inlet port 131a and the outlet port 132a.

Figure 3:
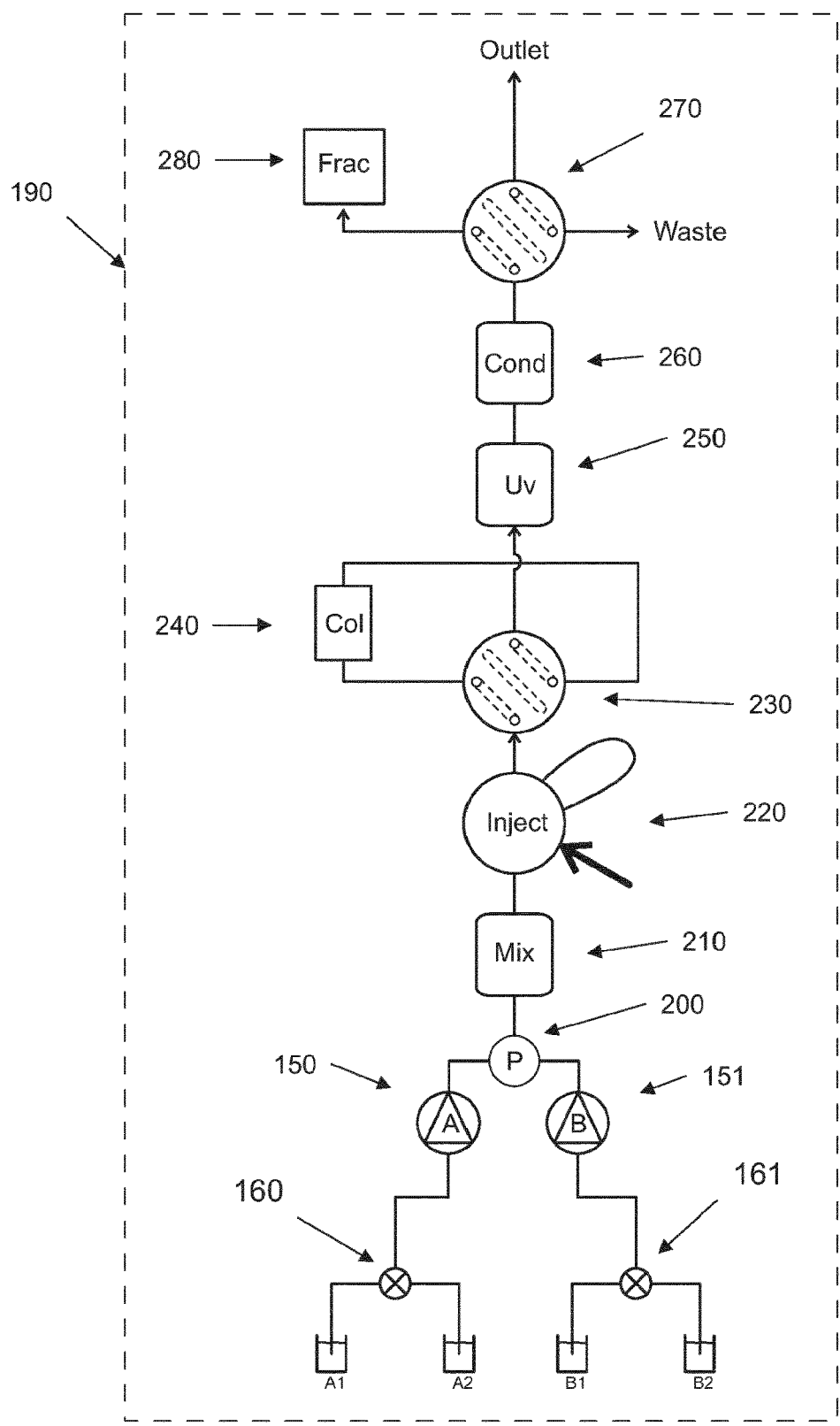
FIG. 3 schematically shows another embodiment of a chromatography system

FIG. 3 schematically shows another embodiment of a chromatography system 190 comprising two input 3-way valves 160 and 161, arranged to select the input fluid from fluid sources A1, A2, B1, B2 for two system pumps 150 and 151. Said chromatography system 190 may further comprise:
- a pressure sensor 200 for registering the system pressure in the flow path after the system pumps,
- a mixer 210 to ensure appropriate mixing of the fluids supplied by the pumps,
- an injection valve 220 for injecting a sample into the fluid path, a column connection valve 230 for selectively connecting/disconnecting a column 240 in the fluid path.

an ultraviolet (UV) monitor 250 for detecting the output from the column.

a conductivity monitor 260, and an output selection valve 270 with two or more output positions, e.g. connected to a fraction collector 280, a waste receptacle or the like.

Figure 6A:
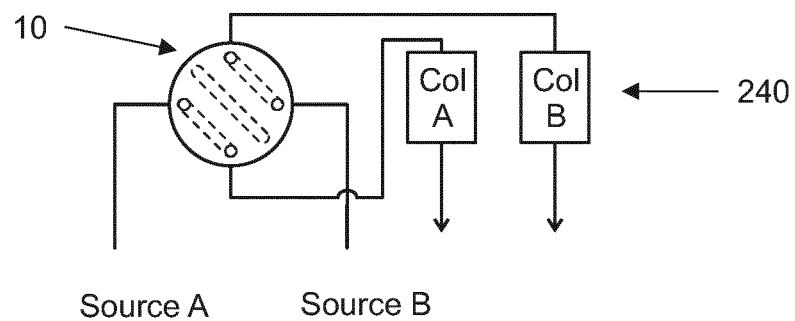
FIGS. 6a and 6b is a schematic view of an alternative employment of the rotary valve.
Figure 6B:
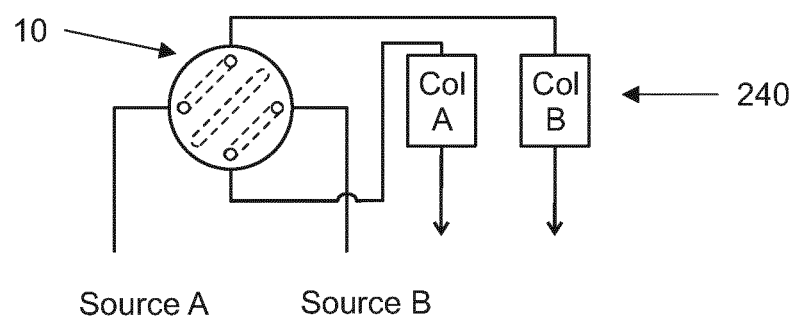
Figure 7A:
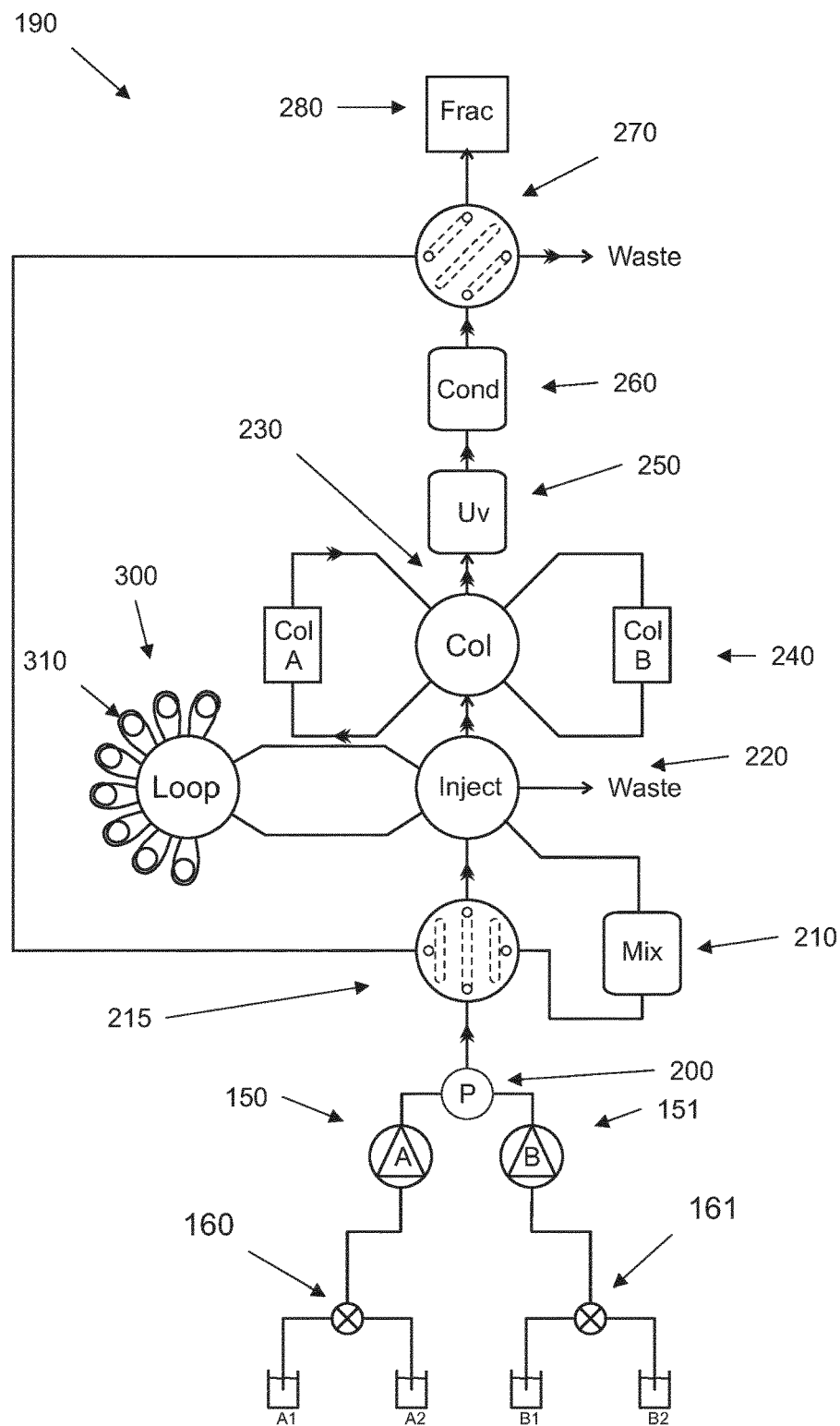
FIGS. 7a and 7b is a schematic view of an alternative employment of the rotary valve.
Figure 7B:
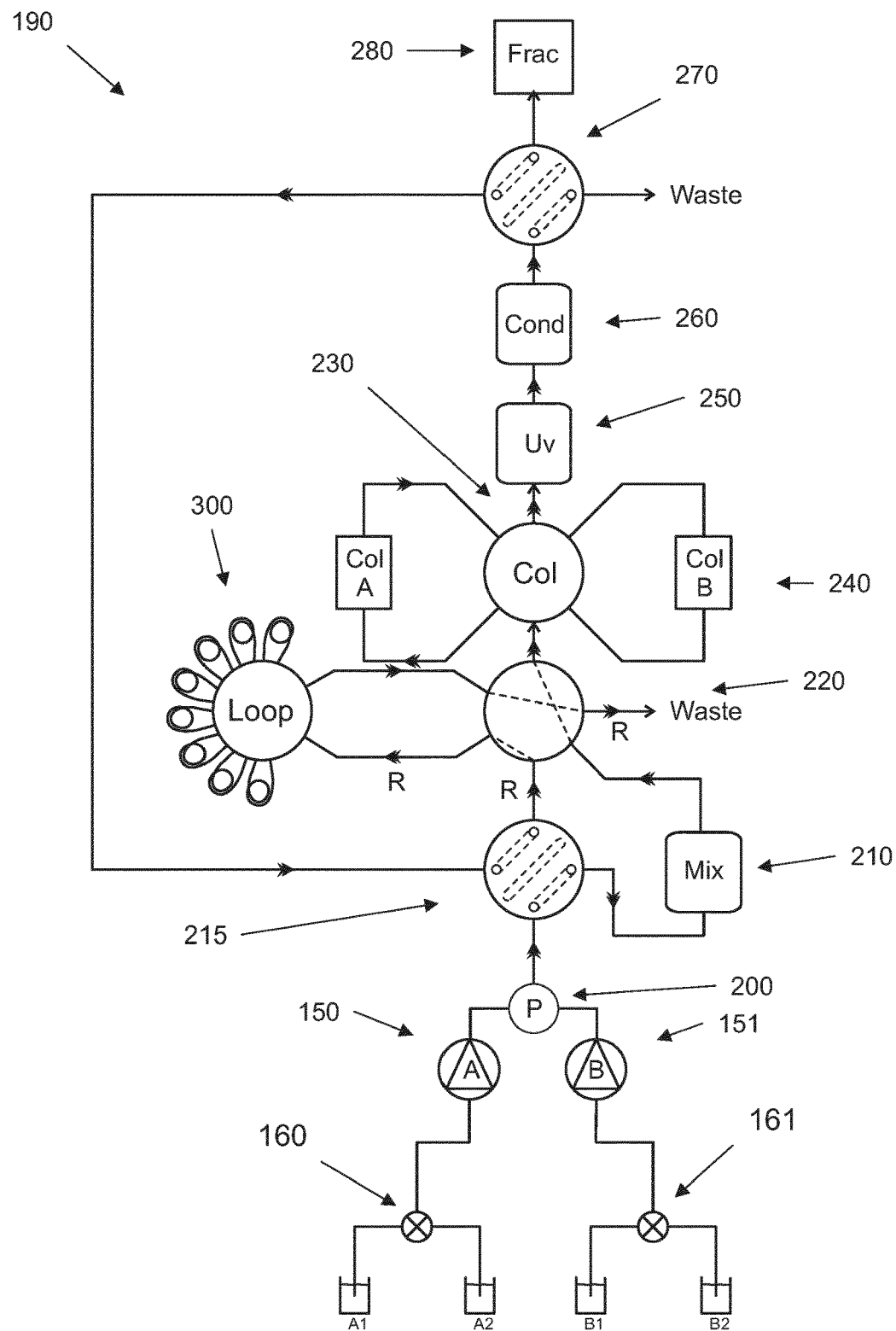

FIG. 3 shows one embodiment of a chromatography system wherein the present valve 10 is used in two different positions, i.e. as column connection valve 230 as is disclosed in FIGS. 6a-6d and as output selection valve 270 as is disclosed in FIGS. 7a-7c.

The chromatography system of FIGS. 1 and 3 represents an example of how a chromatography system may be constructed, and other embodiments may be of different design comprising two or more of some components and potentially lack some of said components. According to one embodiment, the chromatography system is a liquid chromatography system.

Figure 4A:
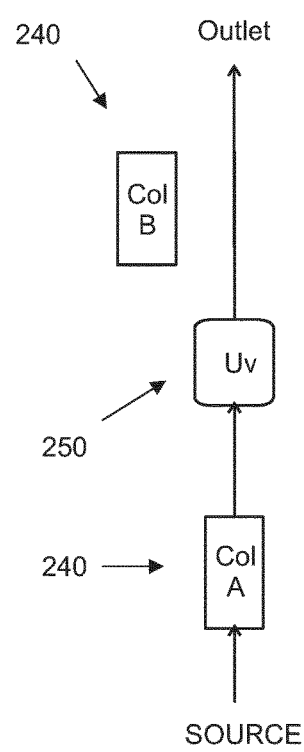
FIGS. 4a to 4c is a schematic view of an alternative employment of the rotary valve.
Figure 4B:
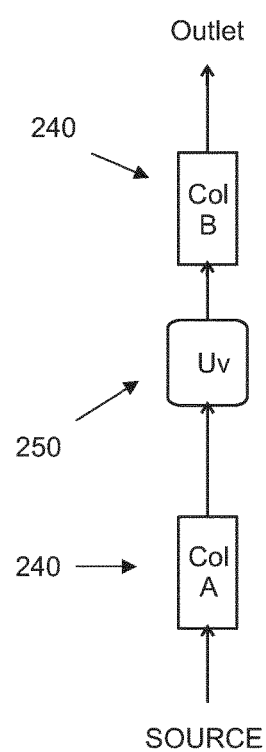
Figure 4C:
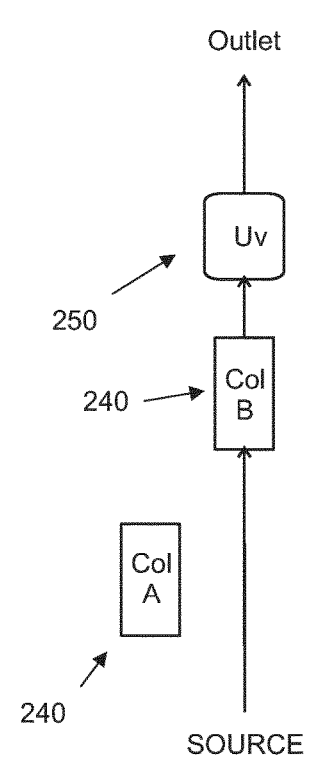

The versatile nature of the rotary valve 10 is further illustrated by some application specific examples where the valve provides substantial benefits in flow path design and over all operation. FIGS. 4a-4c schematically show a two-step purification process which may be simplified by an arrangement using rotary valve 10. In a two-step purification process of this type, the first step shown in FIG. 4a typically involves capture of a target sample such as a protein in a first column A 240, e.g. an affinity column or the like. In order to monitor the capture of the target sample, an UV monitor 250 is connected in the flow path following column A. The capture phase process may conventionally comprise a wash phase wherein non target molecules or the like are washed out from column A, also the wash phase is monitored by the UV monitor to determine when all non-targets have been washed out. During the capture/wash phase, the second column B is not connected as indicated in FIG. 4a. When the output signal from the UV monitor indicates that the capture/wash phase is completed, the next phase is to elute the target sample from column A and further purify it using column B. In order to elute the target sample from col A an elution buffer or the like is supplied to the source whereby the target sample is released from the column A. During the elution phase the output from column A is monitored using the UV monitor to identify when the target sample reaches the UV monitor whereby column B is connected in the fluid path following the UV monitor to receive the target sample, as is shown in FIG. 4b, and then to discontinue the elution process when all target sample is loaded on column B and initiate the third phase which is the second purification step. In the second purification step, as is shown in FIG. 4c, column A is preferably disconnect from the flow path, and the elution buffer is normally replaced with a second purification buffer to drive the chromatographic purification in column B. In this step it is desirable to monitor the output from column B by introducing the UV monitor at the output end of column B. Thus, in the third phase, the logical order of column B and the UV monitor need to be altered compared to the previous step. Unless there are two separate UV monitors available, the process of altering the logical order of two fluidic components is a non trivial operation which requires several valve components. Further, in some situations it is desirable to introduce the eluted target sample from column A onto column B as quickly as possible and then change buffer as quick as possible, e.g. as the buffer used during elution may make the protein unstable.

FIGS. 5a to 5d shows an example of how a two-step purification process may be designed using an arrangement comprising three rotary valves 10a-10c of the present design. In this arrangement, three rotary valves 10a-10c are connected in series source to outlet. A column A 240 is connected between the two component feed and return ports of valve 10a as disclosed in FIGS. 2a to 2d enabling column A to be connected and disconnected from the flow path. A second column B 240 is connected between the component feed ports of the second and third valves 10b and 10c, respectively, and an UV monitor 250 is connected between the component return ports of the second and third valves 10b and 10c, respectively. By this arrangement efficient alternation of the logical order of column B and the UV monitor is enabled using only two valves, while also allowing bypass of both components as well as individual connection of the components to the flow path.

Figure 5A:
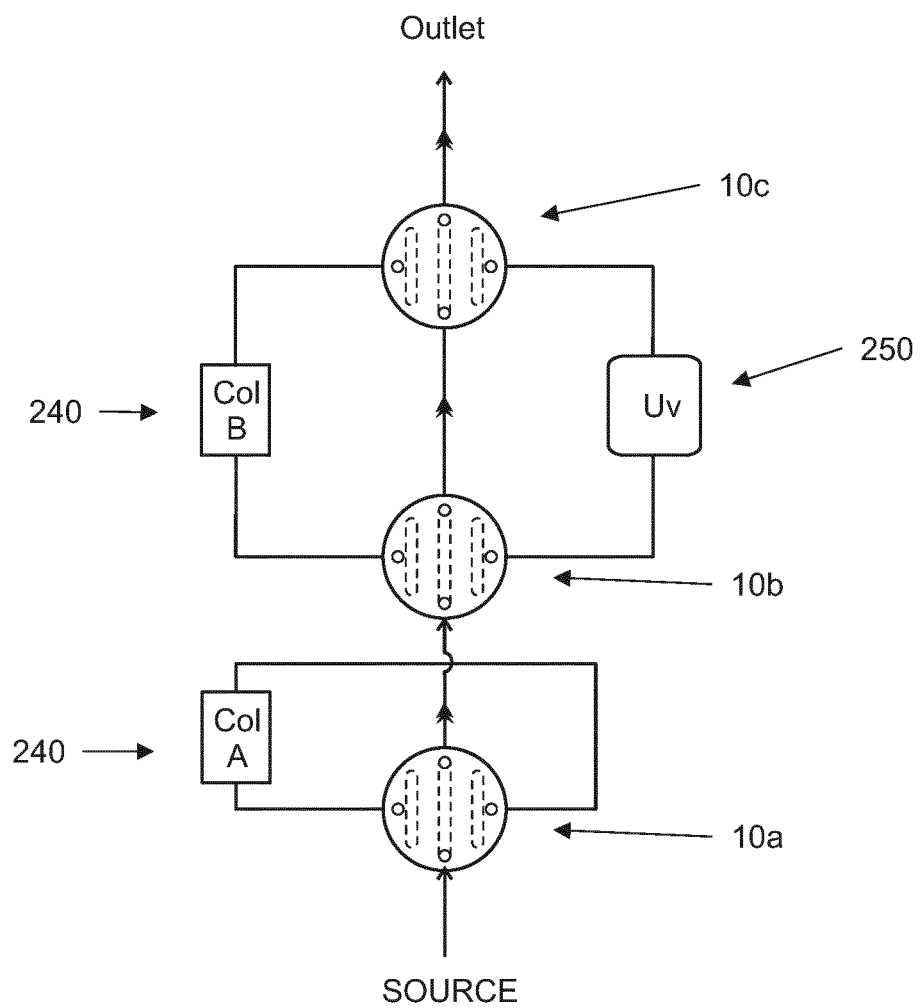
FIGS. 5a-5d schematically show a fluidic circuit for performing the two-step purification process of FIGS. 4a-4c.
Figure 5B:
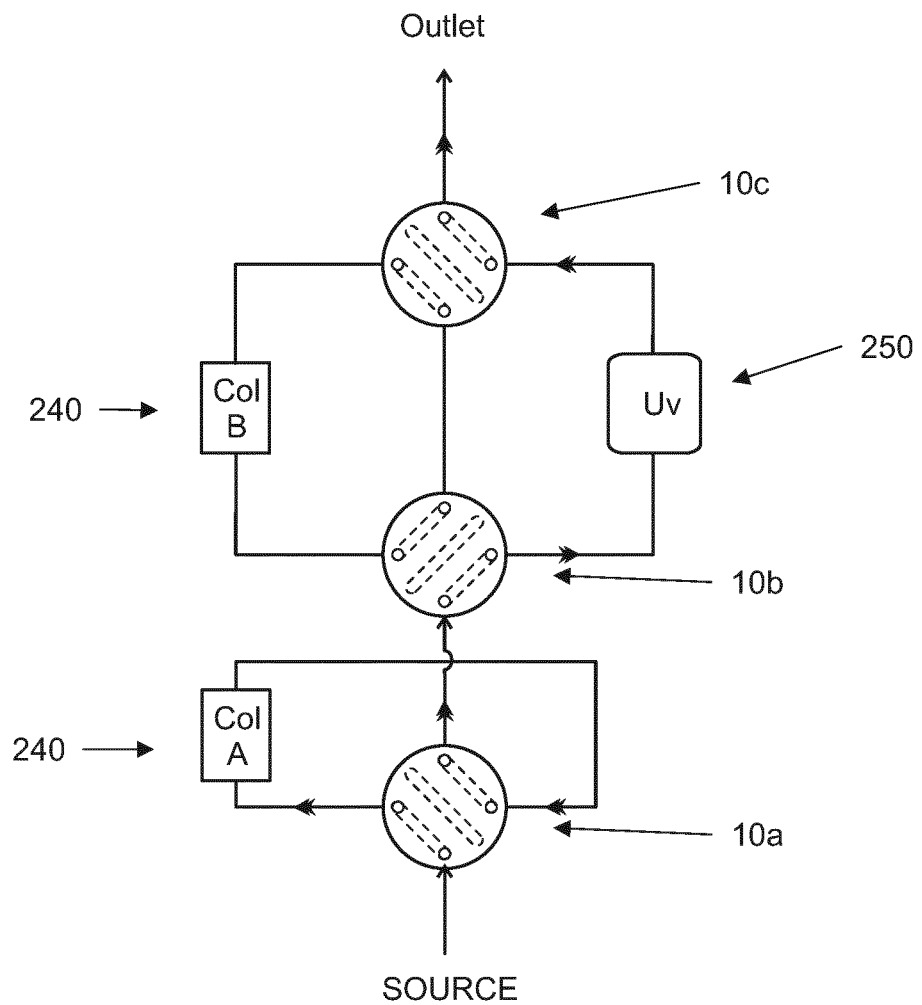
Figure 5C:
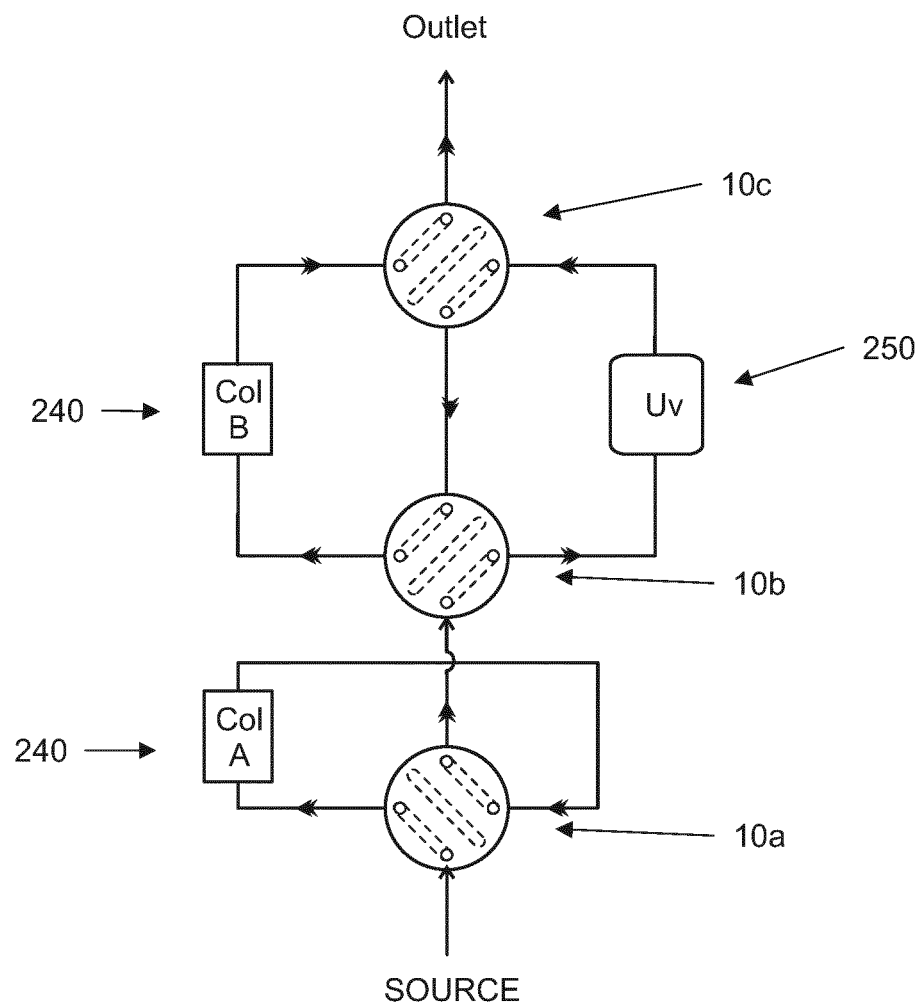
Figure 5D:
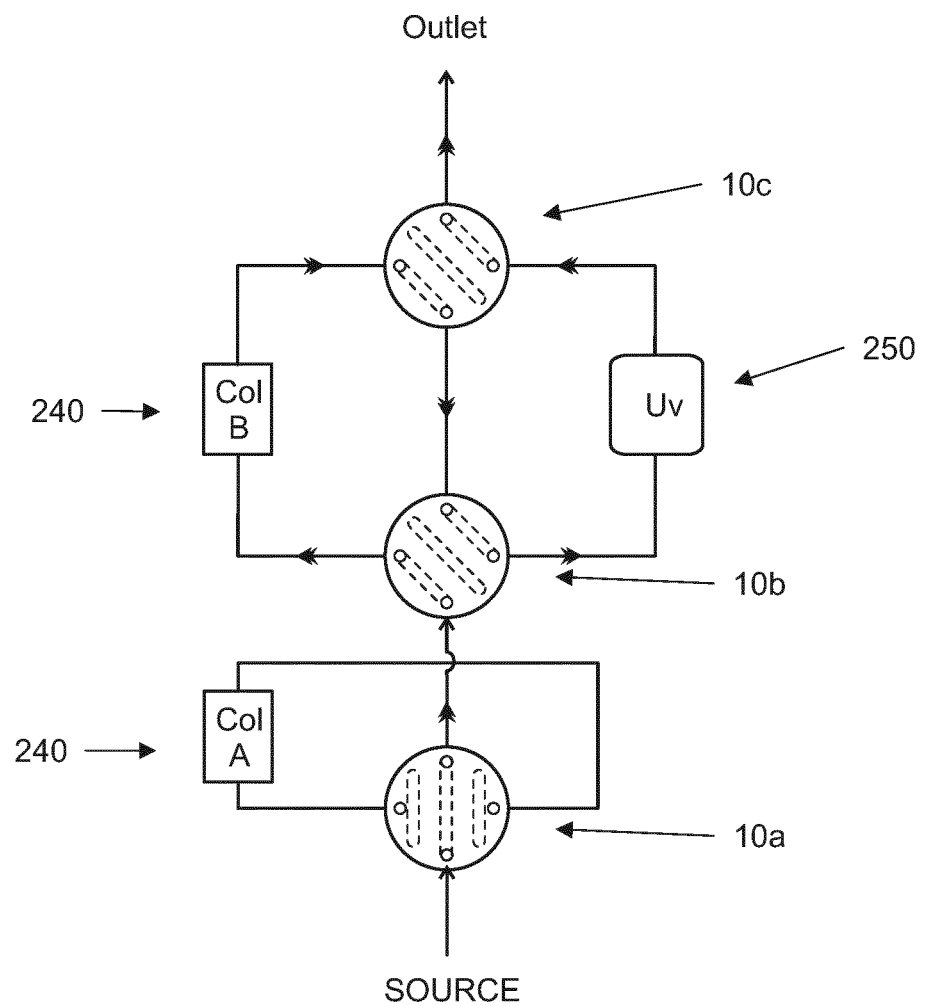

In FIG. 5a all three valves 10a-10c are arranged in bypass mode, first position, whereby the fluid flow goes straight through from the source to the outlet. FIG. 5b represents the capture/wash phase and the initial elution phase wherein the fluid flow is directed through column A and the UV monitor, whereas column B remains disconnected. This is achieved by setting valve 10a in second position, valve 10b in third position and valve 10c in second position. FIG. 5c represents the elution phase where the target sample has been detected by the UV monitor and the second column B has been connected after the UV monitor. This is achieved by keeping valve 10a in second position, keeping valve 10b in third position and setting valve 10c in third position. Note that connection of column B after the UV monitor by switching position of valve 10c from second to third position only. FIG. 5d represents the second purification step where column A is disconnect from the flow path, and the logical order of column B and the UV monitor has been altered. This is achieved by setting valve 10a in first position, valve 10b in second position and valve 10c in second position.

The above embodiment represents one example of use when altering the logical order of components in the flow path is beneficial, this arrangement may further be used in any application wherein this functionality is useful. By altering the logical order of components in the flow path using two valves 10b and 10c connected to two components in accordance with FIGS. 5a to 5d one can create different flow path configurations that optimize the use of available components in each step. E.g. the position of UV monitor, outlet valve or columns can be altered to best suit current application. As is clear from above, such an arrangement for altering the logical order of components in the flow path can generally be achieved by a fluidic circuit comprising a first and a second rotary valves 10a and 10b and a first and a second fluidic component, wherein the inlet port of the second valve is connected to the outlet port of the first valve, the first fluidic component is connected between the component feed port of the first valve and the component feed port of the second valve, and the second fluidic component is connected between the component return port of the first valve and the component return port of the second valve.

Further, the present valve 10 may be used as a switch between two independent fluid paths as is indicated in FIGS. 6a and 6b, wherein a source A and B are connected to the component ports, respectively and column A and B are connected to the inlet and outlet respectively. In this configuration the valve enables selective connection of source A or B to the respective columns A and B. One application where such an arrangement would be useful is to perform conditioning of one column in parallel with running a chromatographic process in the other column, e.g. in a bioprocess production flow path, wherein the conditioned column may be switched into the chromatography process and the other column disconnected for cleaning or replacement.

FIGS. 7a-7b schematically show another application specific example where the present valve 10 is introduced in an alternative position in the flow path of the chromatography system 190 of FIG. 1 in order to enable an alternative two-step purification process wherein eluted sample fractions are stored in sample loops for performing a subsequent second purification step. In the system 190 of FIGS. 7a and 7b a valve 215 has been introduced in the flow path before the injection valve 220 with the outlet port connected to an inlet port of the injection valve 220. The mixer 210 is connected between one of the component ports of valve 215 and a second inlet port on the injection valve 220. The other component port of the valve 215 is connected to an outlet ports of output selection valve 270. Further, in FIGS. 7a and 7b a loop valve 300 is connected to respective outlet and inlet of the injection valve. In the disclosed embodiment, 8 sample loops 310 are shown connected to the loop valve 300 each capable of collecting a sample volume for subsequent purification in accordance with common practice in the field. In an alternative embodiment, the loop functionality may be integrated in the injection valve 220. Compared with FIG. 3, the column selection valve 230 is replaced by a valve capable of connecting two or more columns to the fluid path, illustrated by column A and B 240.

FIG. 7a schematically show the first purification step wherein the target sample is introduced in the fluid path and captured and washed in column A, the liquid flow is indicated by arrows. Like in the above example illustrated in FIGS. 9 and 10, the same setup is initially used for initial elution, optionally with the mixer connected in the flow path. When the first target sample is detected by the UV-monitor 250, valves 215 and 270 are shifted to the respective positions shown in FIG. 7b, whereby a parallel flow path for reintroducing the eluted sample flow into the injection valve 220 is created. During this reinjection process, there are two parallel fluid paths in both valve 215 and the injection valve 220 and the eluted sample flow is directed to the inlet of the loop valve 300 where in desired fractions are collected and stored in the sample loops 310. The valve flow paths in the injection valve 220 are schematically shown as dashed lines in FIG. 7b. As previously mentioned, the eluted fractions stored in the sample loops 310 may subsequently be further purified using column B or the like.

Both embodiments of FIGS. 5a-5d and 7a-7b show examples of how to implement a fully automated two-step purification process using a versatile valve 10 or a valve with similar capabilities.

In another embodiment, wherein some components of the above chromatography setups are rearranged and some additional components are added, it is possible to provide a fully automated two step purification system capable of isolated purifying a plurality of target molecules such as proteins and the like directly from a plurality of cell culture feeds or the like.

This embodiment provides a system capable to both reduce the amount of manual work and to parallelize protein purification to shorten the process time paired with increased robustness and reliability. According to one embodiment, the system may be set up with limited manual interaction and then automatically, and totally unattended, purify a plurality of proteins isolated from each other without further manual interaction. The system setup may further be used in large scale manufacturing of biologics where a breath of different proteins are to be purified isolated from each other for analytical, preparative or ever therapeutic purposes.

In one embodiment, there is provided a system configuration that allows the automated direct-purification of target molecules from a plurality of unclarified antibody feed or the like, e.g. (mAb or polyclonal) containing whole cells wherein the purification of each target molecule from its respective source is kept isolated to avoid contamination by constituents of other feed sources although the same purification units are used in sequence. The system may also be applicable for other affinity based techniques. In embodiments of the present invention it is possible to purify more than one target molecule e.g. (mAb or polyclonal) in an un-attended way. In some embodiments the system configuration allows two step purification and fractionation of multiple target molecule e.g. (mAb or polyclonal) feeds in an un-attended way.

There may further be provided multiple automated safeguards mechanisms to assure a continuous progress of multi mAb-feed purification.

Figure 8:
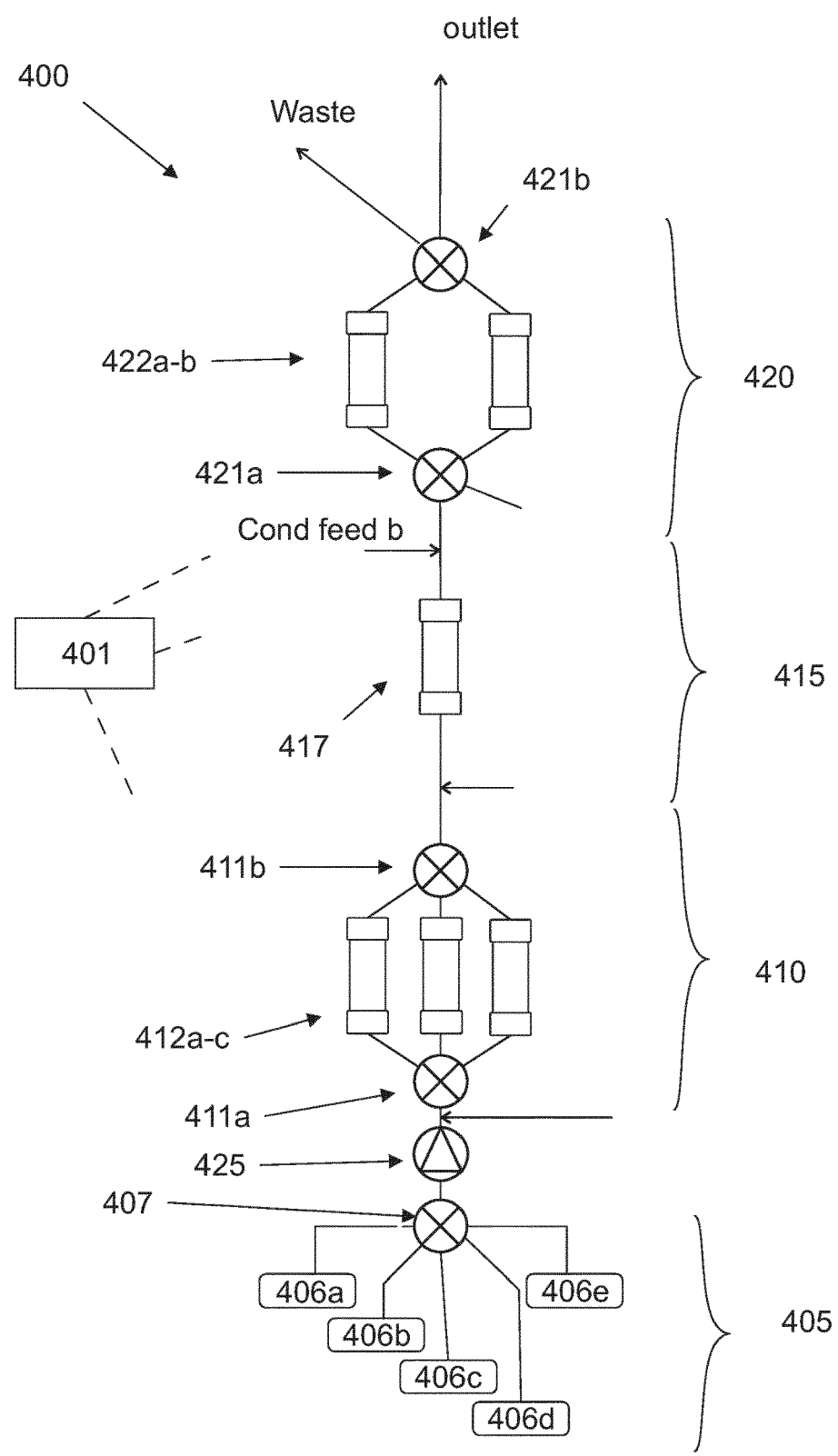
FIG. 8 shows one schematic embodiment of a multi step purification system

According to one embodiment schematically disclosed in FIG. 8 there is provided an automated multi-step chromatography purification system 400 arranged to perform a plurality of isolated multi-step purification cycles for purifying a target molecule from a feed source 406a-e, comprising:

system controller 401 comprising a memory (not shown) storing instructions for controlling the components of the system 400, two or more purification sections 410, 415, 420, each representing a purification step, at least one pump 425 for driving the purification, a valve arrangement with two or more valves 407, 411a,b, 421a,b, for controlling the fluid flow in the system 400 wherein:

one of the purification sections 410 is a capture section with two or more capture columns 412a-c and the valve arrangement 411a,b is arranged for alternately connecting each capture column to a capture flow path wherein the column is fluidically connected to one of the feed sources 406a-e for capturing the respective target molecule, and to an eluent flow path for eluting the captured target molecule to a subsequent purification step and for preparing the column 412a-c for a subsequent capture phase, at least one of the purification sections 415 or 420 subsequent the capture section 410 comprises a smaller number of eluent purification flow paths compared to the number of capture columns, each eluent purification flow paths comprising a purification column 417 or 422a,b, whereby eluent flow from the capture section is sequentially purified in said eluent purification flow paths with intermediate cleaning to keep subsequent purifications isolated, and wherein each purification section being in direct fluidic communication with the subsequent purification section without any intermediate sample storage component.

The automated multi-step chromatography purification system 400 disclosed in FIG. 8 is highly simplified in order to more clearly disclose the main concept of the present invention, and a person skilled in the art would readily understand which features and components would be needed in order to implement the system. More detailed embodiments are shown with reference to FIG. 9 and on. One main characteristic of the automated multi-step chromatography purification system 400 is that it is arranged to automatically perform a plurality multi-step purification cycles for purifying a target molecules from respective feed sources 406a-e in a very efficient way using a limited number of system components and purification units e.g. chromatography columns, while still keeping each target molecule isolated from other molecules or constituents of previous feeds that have been processed by the system in order to avoid contamination between samples. In the context of this invention, the term isolated refers to any degree of chemical isolation required for a specific application to avoid cross talk or cross contamination, and it may be different for different applications. Further it should be noted that the system in accordance with the present invention is arranged to perform the automated multi-step purification without any intermediate sample storage components such as sample loops etc. which is commonly used in the prior art. Instead. each purification section being in direct fluidic communication with the subsequent purification section The system controller 401 may be any type of commonly used controller in the field of automation, e.g. a computer, a tablet device, an embedded processing unit or the like. In order to control the system in accordance with the flow scheme as presented herein, the system controller 401 comprises a memory (not shown) storing instructions for controlling the components of the system 400, and said memory may be any conventional memory available. The system controller 401 is connected to the components of the system by any suitable means like electrical wires, wireless or the like indicated by dashed lines in FIG. 8. and it may further be connected to peripheral units like remote storage devices, computers or the like.

In the multi-step chromatography purification system 400 of FIG. 8 there are three purification sections 410, 415, 420, but as mentioned, multi-step purifications may comprise from two to a plurality of different or similar purification sections, and each one of the section may represent a purification step as is disclosed above and which is appreciated by a person skilled in the art. In FIG. 8 there is schematically disclosed one single pump 425 for driving the purification, but in different implementations of the invention there may any suitable number of pumps as required to provide the automated operation in accordance with the specific set up. Similarly, there is also shown a schematic valve arrangement with a limited number of valves valves 407, 411a,b, 421a,b, for controlling the fluid flow in the system 400, and there may be any suitable number or types of valves. In some embodiments there may be provided multi-port valves that may provide integrated functionality of several fluidic control processes.

According to embodiments of the invention, one of the purification sections 410 is a capture section with two or more capture columns 412a-c as mentioned above, the capture step may be performed by a range of different chromatography technologies. In one embodiment, the capture columns are affinity chromatography columns arranged to capture the proteins of interest. The selection of suitable capture media for the capture columns as well as the selection of the subsequent purification sections is made in accordance with common practice in the field and is e.g. disclosed in the Handbooks of GE Healthcare referred to above. In order to achieve a high throughput, two or more capture columns 412a-c are used in an alternate fashion so that the captured target molecule in one column may be eluted while a subsequent target molecule is captured in another column, or another column is being cleaned in place and equilibrated or the like. As mentioned, in order to keep the target molecules free from contamination, each capture column is prepared for a subsequent capture phase by a cleaning in place process and equilibration process to keep subsequent purifications isolated. Such processes are known in the art per se.

Since the capture step often is more time consuming than subsequent steps, and since the different phases involved, e.g capture, elution and cleaning all need to be performed in sequence the disclosed embodiments have in common that there are a larger number of capture flow paths with capture columns compared to the number of flow paths in subsequent purification sections. However, also subsequent sections may have a plurality of flow paths depending on the characteristics of the specific purification type of said section and the process times involved. Hence the present invention in general terms provides a new way of optimizing the efficiency of multi-step purification processes by providing partly parallelized sections when it is possible to reduce the total cycle time for processing a plurality of sample feeds. Hence in accordance with the embodiment as schematically shown in FIG. 8 the purification sections 415 and 420 subsequent the capture section 410 comprises a smaller number of eluent purification flow paths compared to the number of capture columns.

According to one embodiment, one of the purification sections comprises one or more gel filtration columns, but other column types may be selected as discussed above.

According to one embodiment as is discussed in more detail with respect to the embodiments of FIGS. 9 to 15, the system may comprise a feed filter section arranged in between the feed sources and the capture section, the feed filter section being arranged to selectively introduce a clean filter for each feed flow. It has been shown, that the provision of suitable filters for filtering the feed flow makes it possible to run the multi-step purification process in accordance with the present invention by feed in unclarified cell culture media or lysate directly to the system.

Since some types of purification steps require specific buffer characteristics the system may be provided with an elute conditioning feed source arranged to provide a conditioning flow to the eluent flow in order to change one or more buffer parameters of the elution flow to a condition suitable for a subsequent purification section. In order to protect any subsequent steps from potential precipitations, e.g. due to conditioning of the buffer characteristics, the system may comprise an eluent filter section arranged in between the elute conditioning feed source and the subsequent purification section, the eluent filter section being arranged to selectively introduce a clean filter for each elution flow. The system may further comprise one or more sensors connected to the system controller for providing input of the status of the purification process, the sensors being selected from the group of: pH sensor, conductivity sensor, UV absorption sensor, air sensor, etc.

There is further provided an automated multi-step chromatography purification method comprising a plurality of isolated multi-step purification cycles for purifying a target molecule from a feed source, using an automated chromatography system comprising:

system controller comprising a memory storing instructions for controlling the components of the system, two or more purification sections, each representing a purification step, one of the purification sections is a capture section with two or more capture columns at least one of the purification sections subsequent the capture section comprises a smaller number of eluent purification flow paths compared to the number of capture columns, each eluent purification flow paths comprising a purification column,
wherein each purification section being in direct fluidic communication with the subsequent purification step without any intermediate sample storage component,
at least one pump for driving the purification, and
a valve arrangement with two or more valves for controlling the fluid flow in the system,
wherein the method comprises:
alternately connecting each capture column:
to a capture flow path wherein the column is fluidically connected to one of the feed sources for capturing the respective target molecule, and
to an eluent flow path for eluting the captured target molecule to a subsequent purification step and for preparing the column for a subsequent capture phase,
sequentially purifying the eluent flow from the capture section in said eluent purification flow paths wherein each eluent purification flow path is cleaned
before each subsequent purification to keep the target molecules isolated.

Figure 9:
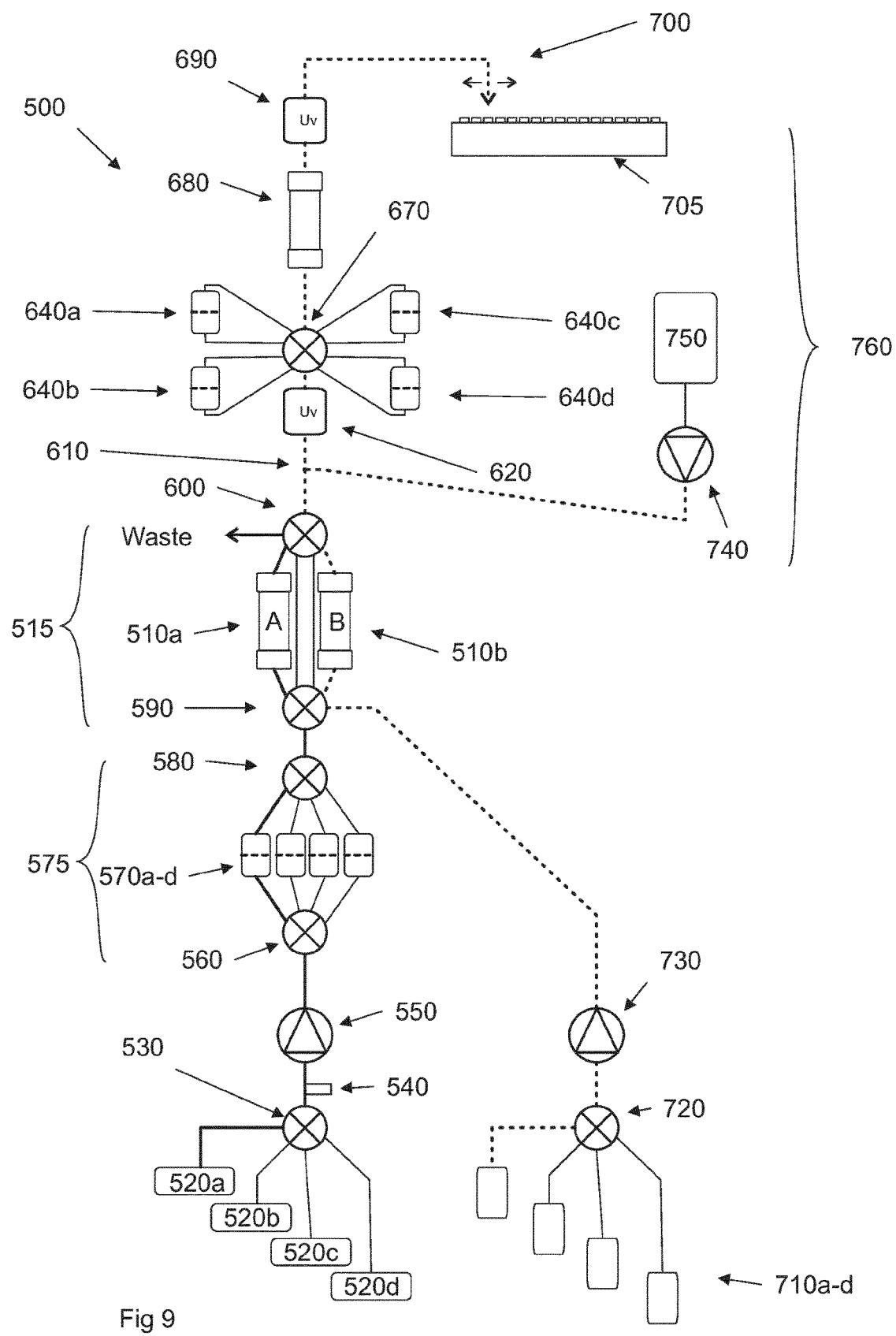
FIG. 9 shows one schematic embodiment of a two step purification system

FIG. 9 shows a schematic illustration of such an automated two step purification system 500 capable of purifying target molecules such as proteins and the like directly from a cell culture or the like. In the following description of the embodiment of FIG. 8 the system is disclosed for purification of mAb from a mAb feed, but as mentioned, the mAb may be any target molecules that may be subject to purification by two step or more chromatography purification.

The configuration includes two independent flows.
Capture flow (solid flow path). Driving the mAb-feed for capturing of mAb on e.g. an affinity column.
Elution flow (dotted flow path). Driving the Elution of mAb from the capture step, loading onto e.g. a gelfiltritation column, gelfilttration and CIP of columns used.

In order to run both the capture run and the elution flows simultaneously two capture columns 510a and 510b are used and which can be switched in between the two flow paths by two capture column valves 590 and 600 respectively e.g. valves 10 as disclosed in FIGS. 6a and 6b, but other valves may be equally useful. The two valves are used to control which one of the two capture columns 510a and 510b that is going to be used for loading feed or elution of mAb. The capability of the valve 10 to handle two parallel flows configurations that makes this possible. In an alternative embodiment, there is provided a multi-functional valve that is arranged to provide the corresponding functionality as provided by two valves in the disclosed embodiment.

Description of the Two Flow Paths.
Capture Flow (Solid Flow Path).
Purpose with this part of the configuration is to in an un-attendant, continuous and isolated manner, harvest the raw antibody feeds and load them onto an affinity column allowing the target molecule of interest to bind to the capture column. Further objective is to allow multiple feeds to be processed, this is achieved by:
First, using an inlet valve that can select what feed to use and also detect when the container is empty and air enters the system. Second using a column valve that can handle multiple filters and direct each feed to a new filter. Column valve is also used to monitoring the condition of the filter by looking at the delta pressure.
The capture flow section of the automated two step purification system 500 disclosed in FIG. 8 comprises:
Four mAb-feed containers 520a-d with unprocessed mAb-feed.
A capture flow inlet valve 530 with at least four inlet ports and one outlet port arranged to:
Select which mAb-feed container 520a-d to use
An air detector 540 arranged to
Trigger change to buffer.
Washing out air that entering the flowpath.
Washing with buffer
a capture flow pump 550 arranged to:
Pump the mAb-feed from the respective mAb-feed containers 520a-d to the capture columns 510a and 510b
A filter selection 575 arranged to filter the unprocessed mAb-feed and to enable selection of a fresh filter 570a-d in response to selection of a new mAb-feed containers 520a-d by the valve capture flow inlet valve 530.
Comprising two filter selection valves 560 and 580 arranged to enable selection of what filter 570a-d to use when filtrating the mAb feed.
Using one filter per mAb-feed, one time use.
According to one embodiment, the filter section is provided with pressure sensors (not shown) arranged to measure pre and post filter pressure to give delta pressure over the filter that e.g. may be used for diagnosing the condition of the filter.
A capture column section 515 comprising:
two capture columns 510a and 510b
a first capture column valve 590, connected to the input end of the capture columns 510a and 510b and arranged to select which capture column 510a and 510b to be used for capturing and elution respectively. As is evident from FIG. 8 and will be disclosed more in detail below, the first capture column valve 590 is arranged such that when one of the two columns is connected in the capture flow position, then the other column is connected in the elution flow position
Optional column control valve (one example shown in FIG. 9) connected between the first capture column valve 590 and each capture column 510a and 510b as disclosed in FIGS. 2a to 2d to enable up-flow, down-flow or by-pass of the capture column 510a and 510b.
a second capture column valve 600, connected to the respective output end of the capture columns 510a and 510b, respectively, and arranged to direct the flow from the capture column 510a or 510b connected for capturing to a waste outlet, and to direct the flow from the capture column 510a or 510b connected for elution to an elution collection flow path (to be disclosed in more detail below).
Sample pump flow is directed to waste.
Elution Flow (Dotted Flow Path).
Purpose of this part of the flow is to in an un-attended, continuous manner elute the target protein captured in the capture column 510a or 510b, adjust buffer condition, detect potential aggregation, protect gelfiltration column by filtration of the eluted target protein, perform a gelfiltration, prepare for a new round by performing column CIP of both columns and re-equilibrate them.
During the elution process, an appropriate elution buffer is provided in a elution buffer source 710a-d, the source being selected by elution selection valve 720. The elution buffer sources 710a-d may e.g. comprise fluids for:

Wash capture
Elution capture
Gelfiltration
CIP

The outlet of the elution selection valve 720 is connected to elution pump 730, which feed the elution buffer to an elution inlet of first capture column valve 590 in the capture column section 515 whereby the elution buffer is fed to the capture column 510a or 510b connected in the elution flow position for elution of the captured species. During the elution process, the outlet of the capture column 510a or 510b connected in the elution flow position is directed by the second capture column valve 600 to an elute purification section 760 arranged to perform a second step purification of the eluted sample. There may further be provided an optional air sensor to prevent air from entering the system (not shown) and a system pressure sensor (not shown) for e.g. monitoring pressure in capture and gelfiltration columns.

The elute purification section 760 comprises an elute conditioning feed source in the form of a buffer adjustment pump 740 for supplying an adjustment buffer from buffer source 750 in order to adjust the buffer parameters of the elution flow. In the disclosed embodiment, the adjustment buffer is introduced into the elution flow at a T intersection 610 whereby the elution flow and the adjustment buffer is mixed, it may however be introduced in any suitable way and the buffers may be mixed actively or passively. The flow rate of the adjustment buffer is controlled so that the resulting mixed elution flow has desirable characteristics for the second purification step. According to one embodiment, elution takes place at low pH and the buffer adjustment pump 740 is used to introduce a buffer into the system flow that will increase the pH to a desired level for the subsequent second purification step. As the introduction of adjustment buffer might result in the formation of aggregates the elute purification section 760 may comprise a sensor 620 for detecting aggregate may be introduced following the adjustment and a filter valve 670 for introducing an aggregate filter 640a-d into the elution flow in response to detection of aggregates in the flow to protect the second purification column 680, e.g. a gelfiltration column. In one embodiment the sensor 620 may be a multi wavelength UV monitor capable of monitoring absorbance at multiple wavelengths. For example monitoring may be performed at 280 nm and 600 nm, whereby 280 nm monitors the presence of protein in the elution flow and 600 nm monitors light scattering caused by potential aggregates.

In the disclosed embodiment, the filter valve 670 is a loop valve rigged with filters in the loop positions, and the filters are placed inline during the time the target protein is eluted from capture and simultaneously loaded onto gelfiltration column. In one embodiment, the filter valve 670 is arranged to bypass the filters 640a-c when no aggregates are detected and during process steps when there is no risk of formation of aggregates etc. e.g. to prevent an increase in backpressure caused by the filter used. In one embodiment during the automated process, prior to the second purification e.g. in the form of gelfiltration, the adjust buffer condition is terminated, the capture column is taken offline and the buffer supplied by the elution pump 730 is changed. The loop valve is used to for selection of what filter to use when sample is eluting from the capture column and simultaneously loaded onto the gelfiltration column. According to one embodiment, to prevent contamination between samples, the same filter is only used for each mAb elution, i.e. one time use. When the mAb peak has entered the gelfiltration column the filter are by-passed.

As already mentioned the second purification unit 680 may be a gelfiltration column of any suitable type, capable of further separating the species eluted from the capture column. Following the second purification unit 680 there may be provided a second UV monitor capable of monitoring absorbance at one or more wavelengths of absorbance of the eluted species and a fraction collector 700 for collecting relevant fractions, e.g. in a multiwall plate 705 or the like. For example monitoring may be performed at 280 nm to monitor the presence of protein in the elution flow. In one embodiment, the second purification 680 and the first UV monitor 620 may be fluidically connected by a valve arrangement as disclosed in FIG. 5a-d or the like to take gelfiltration column and second UV inline offline. When the start of the eluted mAb reach this valve the gelfiltration column will be taken inline, pH-adjustment start, and inline pre-gelfiltration filter taken inline. When the end of the eluted mAb reaches this valve pH adjustment will stop, inline pre-gelfiltration filter taken offinline, capture column taken offline and change off buffer will take place.

Further the system 500 may comprise any suitable sensors, e.g. for conductivity monitoring or pH-monitoring and the like The system is further arranged to perform any required or desired system preparation cycles in between switching from one feed container 520a-d to another in order to start the, such as: washing, conditioning or the like, next purification cycle column CIP and re-equilibration. In the disclosed embodiment, most such cycles are performed by the elution section.

Like in the system of FIG. 1 all active components are connected to a system controller (not shown) connected to pumps and valves for controlling the liquid flow through the system, and to sensors and monitors for monitoring the flow.

Figure 10:
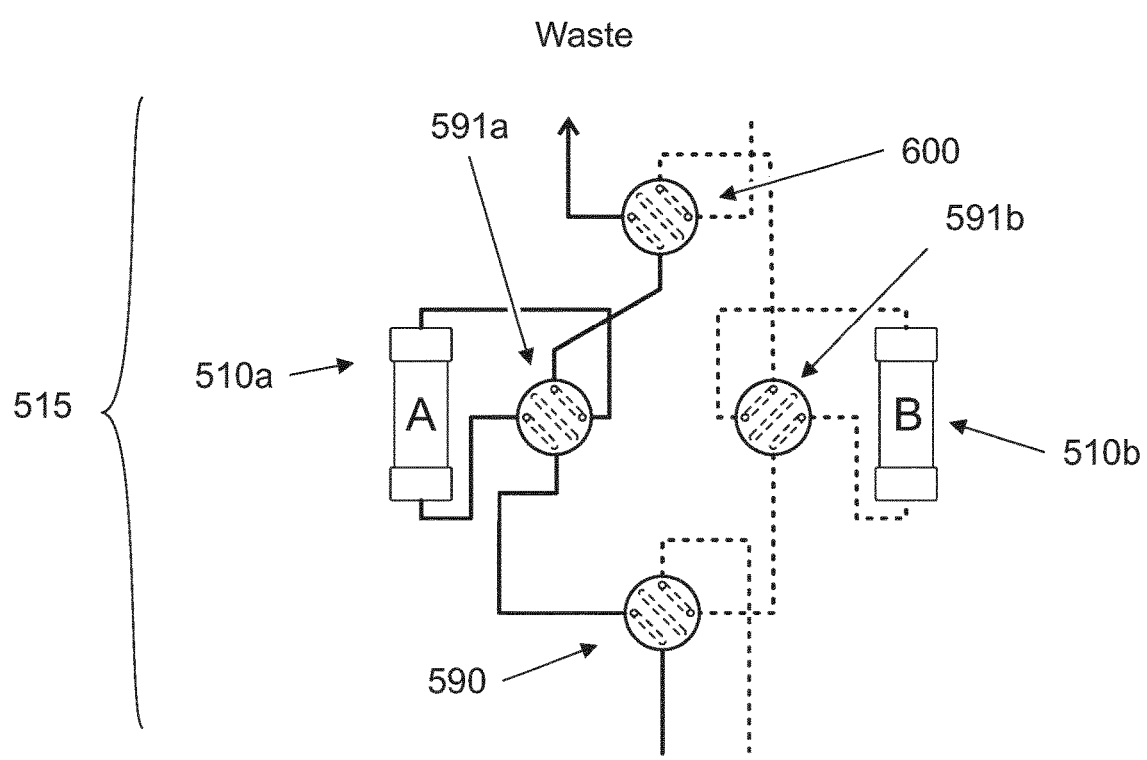
FIG. 10 shows a valve arrangement

FIG. 10 schematically discloses an capture column selection valve arrangement, based on the valve 10 disclosed in FIGS. 2a-d. The arrangement comprises additional column control valves 591a and 591b connected between the first capture column valve 590 and each capture column 510a and 510b as disclosed in FIGS. 2a to 2d to enable up-flow, down-flow or by-pass of the capture column 510a and 510b.

Figure 11:
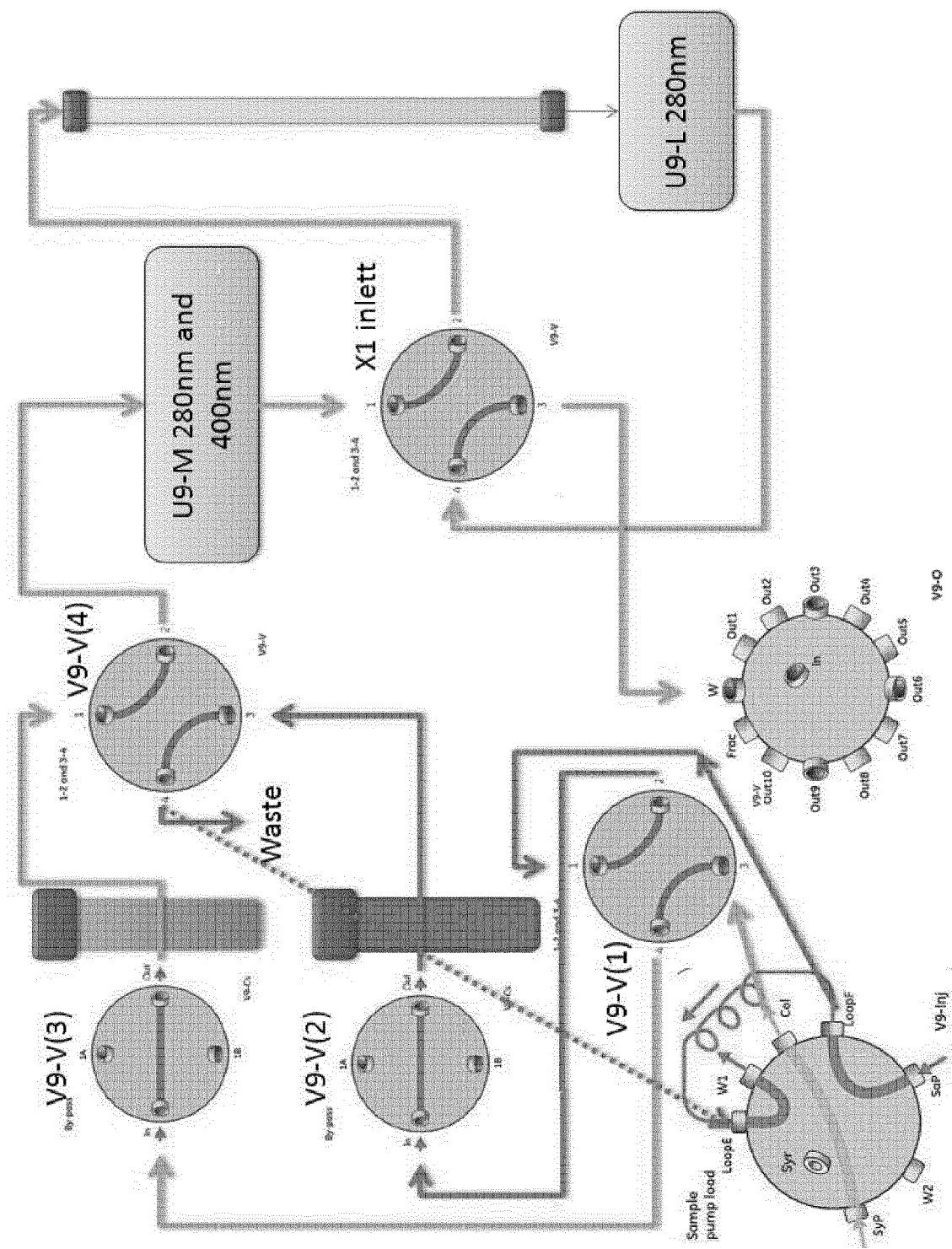
FIG. 11 shows another schematic embodiment of a two step purification system

FIG. 11 shows a schematic example of a flow path arrangement of an automated two step purification process based on an AKTA Pure modular chromatography system from GE Healthcare, wherein reference is made to GE Healthcare product models:

The configuration includes two independent flows.
Sample pump flow (Blue flow path). Driving the mAb-feed for capturing of mAb on affinity column.
System pump flow (Green flow path). Driving the Elution of mAb from the capture step, loading onto gelfiltration column, gelfilttration and CIP of columns used.

In order for both this to run simultaneously two capture columns are used and with the help of two versatile valves V9-V columns we can decide what capture column that is going to be used for loading feed or elution of mAb. It is the ability of the V9-V to handle two parallel flows configurations that makes this possible.

Description of the Two Flow Paths.
Sample pump flow (Blue flow path).
Purpose with this part of the configuration is to in an un-attendant, continues manner harvest the raw antibody feeds and loads them onto an affinity column allowing the target molecule of interest to bind to the capture column. Further objective is to allow multiple feeds to be processed, this is achieved by: First, using an inlet valve that can select what feed to use and also detect when the container is empty and air enters the system. Second using a column valve that can handle multiple filters and direct each feed to a new filter. Column valve is also used to monitoring the condition of the filter by looking at the delta pressure.

Container with unprocessed mAb-feed.
Sample pump inlet valve V9-S
   Selection of what mAb-feed to use
   Detection of air
      Trigger change to buffer.
      Washing out air that entering the flowpath.
      Washing with buffer
Sample pump
   Pumping the mAb-feed
Column valve V9-C
   Selection of what filter to use when filtrating the mAb feed.
   Using one filter per mAb-feed, one time use.
   Measuring pre and post filter pressure.
      Give delta pressure over the filter used for diagnosing the condition of the filter.
Injection valve V9-inj
   Makes it possible to use pump-wash instructions for sample and system pump.
   Direct the flow to correct inlet of V9-V(1)
Versatile valve V9-V(1)
   V9-V(1) is used to select what column to be used for capturing and elution.
Versatile valve V9-V(2) or V9-V(3)
   Acting as column valve, determine up-flow, down-flow or by-pass.
Versatile valve V9-V(4)
   V9-V(4) is used to select if flow is going to waste or entering system flow path.
   Sample pump flow is directed to waste.
Container for waste.
End Sample pump flow.

System Pump Flow (Green Flow Path).
Purpose of this part of the flow is to in an un-attendant, continues manner elute that captured target protein, adjust buffer condition, detect problems with aggregation, protect gelfiltration column by filtration of the eluted target protein, perform a gelfiltration, prepare for a new round by performing column CIP of both columns and re-equilibrate them.

Elution is done by using a inlet valve V9-A to change buffer to elution buffer. All steps are driven by the A-System pump. B-System pump is used for adjust buffer condition after elution. Elution takes place at low pH and the B-system pump is used to introduce a buffer into the system flow that will increase the pH. This might result in the formation of aggregates. To detect aggregate a U9-M capable of monitoring absorbance at multi wavelengths are use. Monitoring at 280 nm and 600 nm are done, 280 nm monitoring the pressens of protein and 600 nm monitoring light scattering caused by aggregates.

To protect the gelfiltration column from aggregates a loop valve rigged with filters are used, those filters are placed inline during the time our target protein is eluted from capture and simultaneously loaded onto gelfiltration column. Then it is taken offline to prevent a increase in backpressure caused by the filter used.

Prior to gelfiltration adjust buffer condition is terminated, capture column are taken offline and change of buffer have taken place. After follow gelfiltration with peak fractionation active.

Last column CIP and re-equilibrate are performed.
Container with buffer for capture wash.
System pump inlet valve V9-A
   Selection of what buffer to use
      Wash capture
      Elution capture
      Gelfiltration
      CIP
   Air sensor to prevent air from entering the system
System pump
   Pumping the buffers
System pressure sensor
   Monitoring pressure in capture and gelfiltration columns
Injection valve V9-inj
   Makes it possible to use pump-wash instructions for sample and system pump.
   Direct the flow to correct inlet of V9-V(1)
Versatile valve V9-V(1)
   V9-V(1) is used to select what column to be used for capturing and elution.
Versatile valve V9-V(2) or V9-V(3)
   Acting as column valve, determine up-flow, down-flow or by-pass.
Versatile valve V9-V(4)
   V9-V(4) is used to select if flow is going to waste or entering system flow path.
   System pump flow is directed to the system flow path.
Inline pH-adjustment
   System pump B flow is used to introduce pH adjusting buffer in the flow path.
   Buffers are mixed actively or passively.
UV and vis monitoring.
   Abs at 280 nm and 600 nm is measured.
      280 nm give information about the protein peak.
      600 nm give information about precipitations that might form.
Loop valve V9-L
   Loop valve is used to for selection of what filter to use when sample is eluting from the capture column and simultaneously loaded onto the gelfiltration column.
      Using one filter per mAb elution, one time use.
      When the mAb peak have entered the gelfiltration column the filter are by-passed.
Versatile valve mapped as X inlet valve.
   This valve is used as a versatile valve to take gelfiltration column and second UV inline offline.
   When the start of the eluted mAb reach this valve the gelfiltration column will be taken inline, pH-adjustment start, and inline pre-gelfiltration filter taken inline.
   When the end of the eluted mAb reaches this valve pH adjustment will stop, inline pre-gelfiltration filter taken offinline, capture column taken offline and change off buffer will take place.
Conductivity monitoring
pH-monitoring
Outlet valve V9-O
   Direct the flow to fraction collector, waste or outlet 1-10
   Handle peak fractionation.
After chromatography are done both columns are CIPed.

Figure 12:
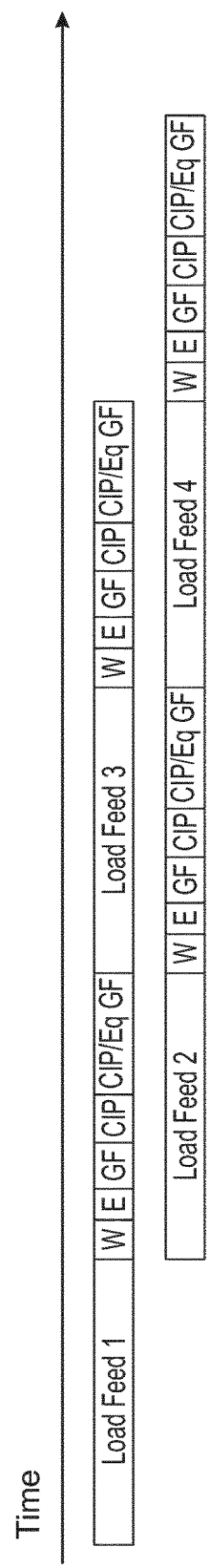
FIG. 12 shows a schematic representation of the various steps of a parallel two step purification process on a system of FIG. 9 or 10.

FIG. 12 schematically show a representation of the parallelized workflow implemented in the embodiment disclosed in FIGS. 9 and 10. In this representation, the top column represents the fluid path that originates through capture column A and the lower column represents the fluid path that originates through capture column B. In this representation the following symbols are used:

Load Feed 1-4⇒capture of target molecule from Feed source 1-4.
W⇒Wash of captured target molecule by buffer flow feed
E⇒Elution of captured target molecule by elution buffer feed
CIP⇒Cleaning in Place of capture column
CIP/Eq⇒Cleaning in Place and Equilibration of gel filtration column As is illustrated in FIG. 12, capture of the target molecule from feed 2 is initialed essentially simultaneously as the capture phase of feed 1 is terminated and so on. In the disclosed example the duration of the capture steps are set to be equal to the total time required for the other steps, but this can obviously be different for different purification setups and steps.

The invention claimed is:

1. An automated multi-step chromatography purification system arranged to perform a plurality of isolated multi-step purification cycles for purifying target molecules from separate feed sources, comprising:
   a system controller comprising a memory storing instructions for controlling components of the system,
   two or more purification sections, each representing a purification step with one of the purification sections being a capture section comprising a first capture column and a second capture column and another one of the purification sections being a subsequent purification section comprising a purification column,
   at least one pump for driving the purification,
   a valve arrangement for controlling the fluid flow in the system, wherein the valve arrangement comprises a source valve connected to the at least one pump,
   a capture flow path, a capture column eluent flow path, and a purification column eluent flow path all share the same source valve,
   wherein: the capture columns and the source valve is arranged to simultaneously
   (i) connecting, through the capture flow path the second capture column to one of the separate feed sources for capturing the respective target molecule, and
   (ii) eluting, through the capture column eluent flow path a captured target molecule from the first capture column to the purification column and for preparing the eluted first capture column for a subsequent capture phase,
   wherein the subsequent purification section comprises a smaller number of purification column eluent flow paths compared to the number of capture columns, each purification column eluent flow path comprising a purification column, whereby eluent flow from each of the capture column is separately purified in said purification column eluent flow path with intermediate cleaning of the purification column eluent flow path to keep subsequent purifications isolated, and
   wherein each purification section being in direct fluidic communication with the subsequent purification section without an intermediate sample storage component.

2. The system according to claim 1 wherein the capture column is an affinity chromatography column.

3. The system according to claim 1 wherein the subsequent purification section comprises one or more gel filtration columns.

4. The system according to claim 1 further comprising a feed filter section arranged in between the feed sources and the capture section, the feed filter section being arranged to selectively introduce a clean filter for each feed flow.

5. The system according to claim 1 further comprising an elute conditioning feed source arranged to provide a conditioning flow to the eluent flow in order to change one or more buffer parameters of the elution flow to a condition suitable for a subsequent purification section.

6. The system according to claim 1 further comprising an eluent filter section arranged in between the elute conditioning feed source and the subsequent purification section, the eluent filter section being arranged to selectively introduce a clean filter for each elution flow.

7. The system according to claim 1 further comprising one or more sensors connected to the system controller for providing input of the status of the purification process, the sensors being selected from the group of; pH sensor, conductivity sensor, UV absorption sensor, air sensor.

8. The system according to claim 1 being arranged to prepare the capture columns for a subsequent capture phase by a cleaning in place process and equilibration process to keep subsequent purifications isolated.

9. The system according to claim 1 wherein the intermediate cleaning of the eluent purification flow paths comprises a cleaning in place process and equilibration process.

10. An automated multi-step chromatography purification method comprising a plurality of isolated multi-step purification cycles for purifying target molecules from separate feed sources, using an automated chromatography system that comprises:
   a system controller comprising a memory storing instructions for controlling the components of the system,
   two or more purification sections, each representing a purification step and being in direct fluidic communication with the subsequent purification step without any intermediate sample storage component, comprising:
   i. a capture section comprising a first capture column and a second capture column, and
   ii. a subsequent purification sections that is subsequent to the capture section and comprises a smaller number of purification column eluent flow paths compared to the number of capture columns, each purification column eluent flow paths comprising a purification column,
   at least one pump for driving the purification, and
   a valve arrangement for controlling the fluid flow in the system, wherein the valve arrangement comprises a source valve connected to the at least one pump,
   a capture flow path, a capture column eluent flow path, and a purification column eluent flow path all share the same source valve,
   the method comprising:
   (i) capturing, through the capture flow path, a target molecule onto the second capture column, and
   (ii) simultaneously eluting, through the capture column eluent flow path, a captured target molecule from the first capture column, and preparing the eluted first capture column for a subsequent capture phase,
   separately purifying each eluent flow from the capture section in one of said purification column eluent flow paths, and intermediate cleaning each purification column eluent flow path before each subsequent purification to keep the target molecules isolated.

11. The method according to claim 10 wherein the capture column is an affinity chromatography column.

12. The method according to claim 10 wherein one of the purification sections comprises one or more gel filtration columns.

13. The method according to claim 10 further comprising a filtration step using a feed filter section arranged in between the feed sources and the capture section, the feed filter section being arranged to selectively introduce a clean filter for each feed flow.

14. The method according to claim 10 further comprising a step of using an elute conditioning feed source arranged to provide a conditioning flow to the eluent flow in order to change one or more buffer parameters of the elution flow to a condition suitable for a subsequent purification section.

15. The method according to claim 10 further comprising a filtration step using an eluent filter section arranged in between the elute conditioning feed source and the subsequent purification section, the eluent filter section being arranged to selectively introduce a clean filter for each elution flow.

16. The method according to claim 10 wherein the chromatography system further comprises one or more sensors connected to the system controller for providing input of the status of the purification process, the sensors being selected from the group of: pH sensor, conductivity sensor, UV absorption sensor, air sensor.

17. The method according to claim 10 wherein the step of preparing the capture columns for a subsequent capture phase comprises implementing a cleaning in place process and equilibration process to keep subsequent purifications isolated.

18. The method according to claim 10 wherein the intermediate cleaning of the eluent purification flow paths comprises a cleaning in place process and equilibration process.

19. An automated multi-step chromatography purification system arranged to perform a plurality of isolated multi-step purification cycles for purifying target molecules from separate feed sources, comprising:
   a system controller comprising a memory storing instructions for controlling the components of the system,
   two or more purification sections, each representing a purification step with one of the purification sections being a capture section comprising a first affinity chromatography (AC) column and a second AC column and another one of the purification sections being a subsequent purification section comprising a gel filtration purification (GF) column,
   at least one pump for driving the purification,
   a valve arrangement for controlling the fluid flow in the system, wherein the valve arrangement comprises a source valve connected to the at least one pump,
   a capture flow path, an AC column eluent flow path, and a GF column eluent flow path all share the same source valve,
   wherein: the AC columns and the source valve is arranged to simultaneously
   (i) connecting, through the AC flow path the second AC column to one of the separate feed sources for capturing the respective target molecule, and
   (ii) eluting, through the AC column eluent flow path a captured target molecule from the first AC column to the GF column and for preparing the eluted first AC column for a subsequent capture phase,
   wherein the subsequent purification section comprises a smaller number of GF eluent flow paths compared to the number of AC columns, each GF eluent flow paths comprising a GF column, whereby eluent flow from each of the capture column is separately purified in said GF eluent flow path with intermediate cleaning of the GF eluent flow paths to keep subsequent purifications isolated, and
   wherein each purification section being in direct fluidic communication with the subsequent purification section without an intermediate sample storage component.

20. An automated multi-step chromatography purification method comprising a plurality of isolated multi-step purification cycles for purifying target molecules from separate feed sources, using the automated chromatography system of claim 19,
   the method comprising:
   (i) capturing, through the AC flow path, a target molecule onto the second AC column, and
   (ii) simultaneously eluting, through the AC column eluent flow path, a captured target molecule from the first AC column, and preparing the eluted first AC column for a subsequent capture phase,
   separately purifying each eluent flow from the capture section in one of said GF eluent flow paths, and
   intermediate cleaning each GF eluent flow path before each subsequent purification to keep the target molecules isolated.

* * * * *